US010036668B2

(12) United States Patent
Nagai

(10) Patent No.: US 10,036,668 B2
(45) Date of Patent: Jul. 31, 2018

(54) COLORIMETER AND COLORIMETRY METHOD

(71) Applicant: Konica Minolta, Inc., Tokyo (JP)

(72) Inventor: Yoshiroh Nagai, Hyogo (JP)

(73) Assignee: Konica Minolta, Inc., Tokyo (JP)

( * ) Notice: Subject to any disclaimer, the term of this patent is extended or adjusted under 35 U.S.C. 154(b) by 12 days.

(21) Appl. No.: 15/310,695

(22) PCT Filed: Apr. 23, 2015

(86) PCT No.: PCT/JP2015/062444
§ 371 (c)(1),
(2) Date: Nov. 11, 2016

(87) PCT Pub. No.: WO2015/174244
PCT Pub. Date: Nov. 19, 2015

(65) Prior Publication Data
US 2017/0082493 A1    Mar. 23, 2017

(30) Foreign Application Priority Data

May 13, 2014 (JP) ................................. 2014-099245

(51) Int. Cl.
| | |
|---|---|
| *G06K 9/00* | (2006.01) |
| *G01J 3/52* | (2006.01) |
| *G01J 3/46* | (2006.01) |
| *G06T 1/00* | (2006.01) |
| *G06T 7/11* | (2017.01) |
| *G06T 7/77* | (2017.01) |
| *G06T 7/13* | (2017.01) |
| *G06T 7/90* | (2017.01) |
| *G01N 21/25* | (2006.01) |
| *G06K 9/62* | (2006.01) |

(Continued)

(52) U.S. Cl.
CPC . *G01J 3/52* (2013.01); *G01J 3/46* (2013.01);
*G01N 21/251* (2013.01); *G06K 9/6267*
(2013.01); *G06T 1/00* (2013.01); *G06T 7/0004*
(2013.01); *G06T 7/11* (2017.01); *G06T 7/13*
(2017.01); *G06T 7/77* (2017.01); *G06T 7/90*
(2017.01); *G06T 11/206* (2013.01); *G06T 2207/30144* (2013.01)

(58) Field of Classification Search
CPC ................ G06T 7/00; G01J 3/00; G06K 9/00
USPC .......................................... 382/112; 358/504
See application file for complete search history.

(56) References Cited

U.S. PATENT DOCUMENTS 6,765,674 B2 * 7/2004 Orelli ........................ G01J 3/02
356/402
9,671,289 B2 * 6/2017 Nagai ........................ G01J 3/50

FOREIGN PATENT DOCUMENTS

CN          103728023 A       4/2014

OTHER PUBLICATIONS

International Search Report issued in corresponding application No. PCT/JP2015/062444 dated Jul. 28, 2015 (4 pages).
(Continued)

*Primary Examiner* — Abolfazl Tabatabai
(74) *Attorney, Agent, or Firm* — Osha Liang LLP

(57) ABSTRACT

A color measurement device obtains edge information based on an image of a color chart. The color measurement device statistically processes the edge information to obtain edge statistic information. Based on the edge information and the edge statistic information, the color measurement devices obtains the position of each patch of a number of patches of the color chart.

8 Claims, 16 Drawing Sheets

(51) Int. Cl.
*G06T 7/00* (2017.01)
*G06T 11/20* (2006.01)
*H04N 1/46* (2006.01)

(56) References Cited

OTHER PUBLICATIONS

Written Opinion of the International Searching Authority issued in corresponding application No. PCT/JP2015/062444 dated Jul. 28, 2015 (3 pages).
Office Action issued in corresponding Chinese Application No. 201580024778.9 dated Aug. 18, 2017 (9 pages).

\* cited by examiner

STREAK-LIKE PRINTING IRREGULARITY

EG

EGerr
ERRONEOUSLY-DETECTED LINE DUE
TO STREAK-LIKE PRINTING IRREGULARITY

EG  CL     EGerr  CLest

EG  CL     EGerr

COLORIMETER AND COLORIMETRY METHOD

TECHNICAL FIELD

The present invention relates to a color measurement device and method for measuring a color, and more particularly to a color measurement device and method capable of measuring a color at a proper position automatically.

BACKGROUND

In a company specializing in creating color printed materials, such as a printing company, in order to maintain quality of printed materials, colors of a printed material are measured to adjust colors of a printing unit which has printed the printed material, on a regular basis. In such color adjustment for a printing unit, as one example, original image data, called "color chart", is printed by the printing unit, and respective colors of a plurality of patches in the printed color chart are measured by a color measurement device. Then, an amount of color deviation between an actual measured value and a target value of a color of each patch is evaluated, and, according to a result of the evaluation, colors of the printing unit are adjusted.

The color chart is constructed such that it comprises a plurality of color samples, called "patches", as mentioned above, wherein each of the patches are formed differently in terms of color (hue, brightness (luminosity), chroma (colorfulness, saturation)), and arranged in a given manner. Such a color chart includes various types. For example, there is one type of color chart constructed such that a plurality of quadrangular-shaped patches having various colors are arranged in horizontal and vertical directions in a two-dimensional array configuration. In this type of color chart, depending on intended contents of the evaluation, there are various patterns, such as a pattern in which the patches are arranged to form a random (arbitrary) color array, and a pattern in which the patches are arranged such that a change in shade between adjacent ones of the patches becomes smaller, like a gradation. This type of color chart includes not only a color chart which is created by a user using a color chart creation tool provided from a manufacturer of color measurement devices, but also a color chart which is provided from a public agency. As above, a color chart can have a significantly wide variety of patterns by differences in shape, arrangement, color combination and others of the patches.

Meanwhile, the number of colors for use in color adjustment for a printing unit has been increasing year after year. Accordingly, the number of patches arranged in a color chart has also been increasing, wherein a size (area) of each patch is relatively small.

From such a circumstance, it has become practically impossible to manually accurately adjust a position of a measuring section of a color measurement device with respect to each patch, so as to perform a color measurement. For this reason, there is a need for an automatic system for automatically measuring a position of each patch, and automatically adjusting a position of the measuring section of the color measurement device to become coincident with the measured position of the patch, so as to measure a color of the patch. As one example of this system, Gretag-Macbeth AG proposed a method which comprises: taking a two-dimensional color image of a color chart to be measured; calculating a position of each patch by an image processing technique using a computer; and moving a color measuring head to the determined position of the patch so as to measure colors of the color chart, as described in the following Patent Literature 1.

In this regard, when a position of each patch is derived from the taken image of the color chart by image processing, detection of the position of each patch is likely to become impossible, depending on the type of color chart. Particularly, in the case where a position of each patch of a color chart is detected based on an edge of the patch, and the color chart includes a gradation pattern, a portion of the color chart consisting of the gradation pattern can includes a patch whose edge region has a small difference in color density. In this case, an edge of such a patch cannot be detected and therefore a position of this patch cannot be accurately detected.

CITATION LIST

Patent Literature

Patent Literature 1: U.S. Pat. No. 6,765,674 B

SUMMARY OF INVENTION

One or more embodiments of the invention provide a color measurement device and method capable of more accurately detecting a position of a patch to measure a color of the patch at a more proper position.

In a color measurement device and method of the present invention, given information regarding an edge is derived as edge information based on an image of a color chart by an edge information processing section, and the derived edge information is statistically processed by an edge statistic processing section, to thereby derive a given edge statistic. Then, based on the edge information and the edge statistic, respective positions of a plurality of patches are derived by a patch position processing section. Thus, the color measurement device and method of the present invention make it possible to more accurately detect a position of a patch to measure a color of the patch at a more proper position.

These and other objects, features, and advantages of the present invention will become apparent upon reading of the following detailed description along with the accompanying drawings.

DETAILED DESCRIPTION

Based on the drawings, in accordance with one or more embodiments of the present invention will now be described. It should be noted that elements or components assigned with the same reference sign in the figures means that they are identical, and therefore duplicated description thereof will be omitted appropriately. In this specification, for a generic term, a reference sign without any suffix is assigned thereto, and, for a term meaning an individual element or component, a reference sign with a suffix is assigned thereto.

Figure 1:
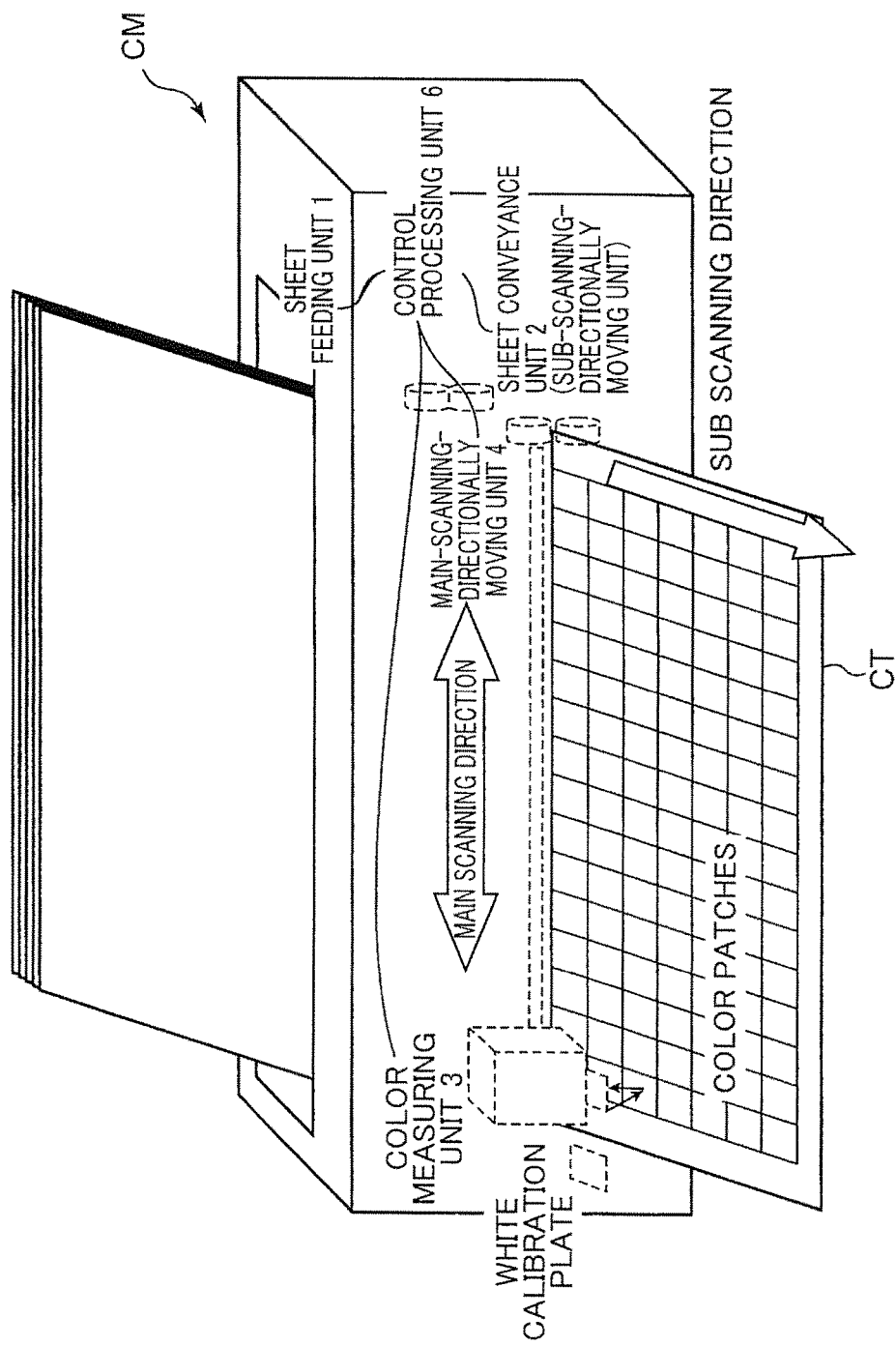
FIG. 1 is a perspective view depicting a schematic configuration of a color measurement device in accordance with one or more embodiments of the invention.
Figure 2:
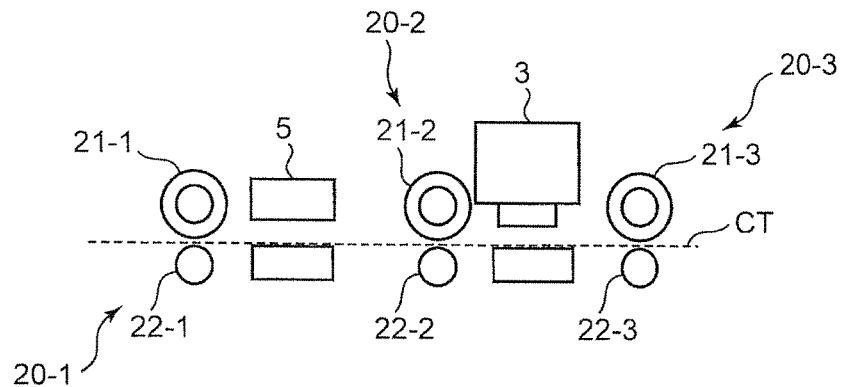
FIG. 2 is a schematic side view depicting an arrangement relationship between an imaging unit and a color measuring unit in the color measurement device in accordance with one or more embodiments of the invention.
Figure 3:
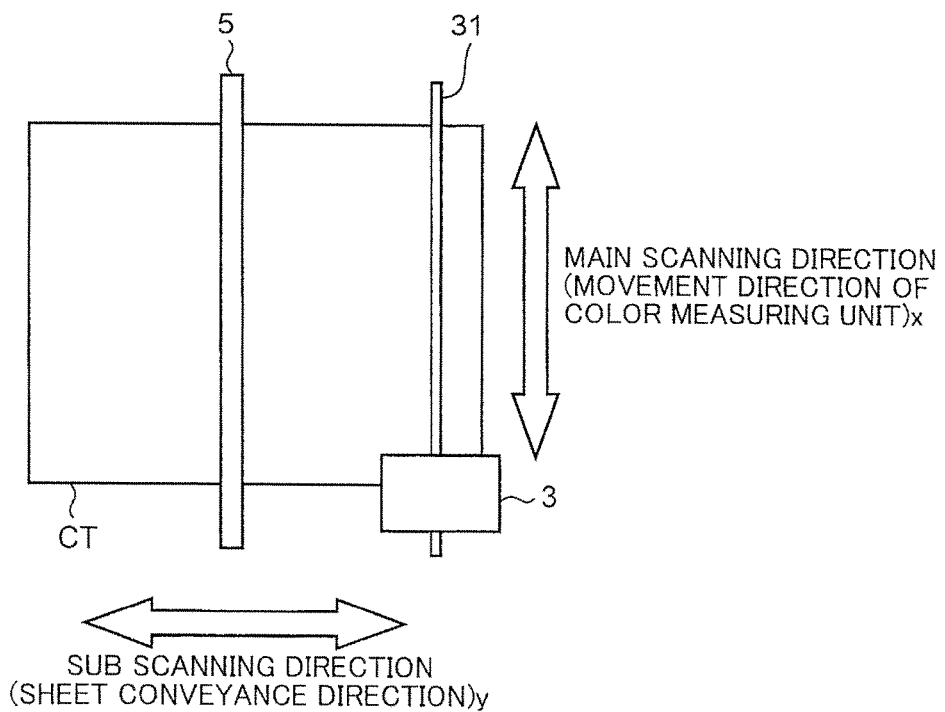
FIG. 3 is a schematic top view depicting the arrangement relationship between the imaging unit and the color measuring unit in the color measurement device in accordance with one or more embodiments of the invention.
Figure 4:
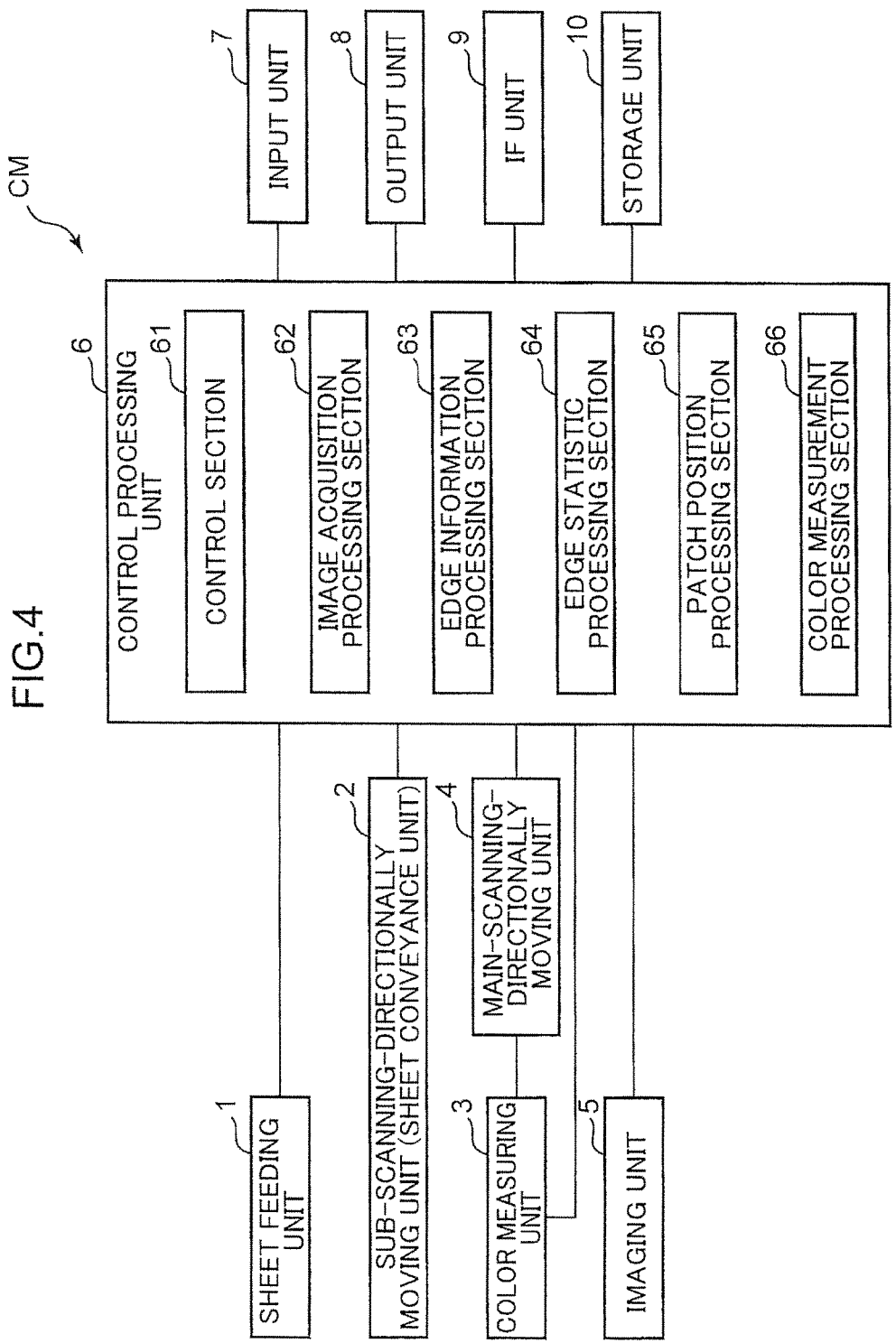
FIG. 4 is a block diagram depicting an electrical configuration of the color measurement device in accordance with one or more embodiments of the invention.

FIG. 1 is a perspective view depicting a schematic configuration of a color measurement device in accordance with one or more embodiments. FIG. 2 is a schematic side view depicting an arrangement relationship between an imaging unit and a color measuring unit in the color measurement device in accordance with one or more embodiments. FIG. 3 is a schematic top view depicting the arrangement relationship between the imaging unit and the color measuring unit in the color measurement device in accordance with one or more embodiments. FIG. 4 is a block diagram depicting an electrical configuration of the color measurement device in accordance with one or more embodiments.

A color measurement device in accordance with one or more embodiments of the invention is a device for measuring a color (hue, brightness (luminosity), chroma (colorfulness, saturation)) of a measurement target, and includes: a color measuring unit which measures a color; an imaging unit which acquires an image; an image acquisition processing section which causes the imaging unit to image a color chart having a plurality of patches each of which is a region of a given color, to thereby acquire an image of the color chart; an edge information processing section which derives given information regarding an edge as edge information, based on the image of the color chart acquired by the edge information processing section; an edge statistic processing section which statistically processes the edge information derived by the edge information processing section, to thereby derive a given statistic regarding the edge as an edge statistic; a patch position processing section which derives respective positions of the plurality of patches, based on the edge information derived by the edge information processing section and the edge statistic derived by the edge statistic processing section; and a color measurement processing section which causes the color measuring unit to measure respective colors of the plurality of patches, at the respective positions of the plurality of patches derived by the patch position processing section. In one or more embodiments, the color measurement device further includes a conveyance unit which conveys the color chart, and a moving unit which moves the color measuring unit. In this color measurement device, edge information is derived from the image of the color chart by the edge information processing section, and an edge statistic is derived from the derived edge information by the edge statistic processing section. Then, based on the edge information and the edge statistic, respective positions of the plurality of patches are derived by the patch position processing section. That is, the color measurement device in accordance with one or more embodiments is operable to derive a position of each patch, based on the edge information and the edge statistic, instead of based only on the edge information. Thus, for example, erroneous detection (false detection) of an edge, undetection (miss direction) of an edge or the like can be reduced, so that it becomes possible to more accurately detect the position of each patch and measure a color of each patch at more proper position.

More specifically, for example, the color measurement device CM in accordance with one or more embodiments includes a sheet feeding unit 1, a sub-scanning-directionally moving unit (sheet conveyance unit) 2, a color measuring unit 3, a main-scanning-directionally moving unit 4, an imaging unit 5, a control processing unit 6, an input unit 7, an output unit 8, an interface unit (IF unit) 9, and a storage unit 10, as depicted in FIGS. 1 to 4.

The sheet feeding unit 1 is a sheet conveying mechanism which is connected to the control processing unit 6 and is operable, according to control of the control processing unit 6, to introduce a measurement target sheet set in the color measurement device CM, into an inside of the color measurement device CM. The measurement target sheet may be any type. For example, in the case of adjusting colors of a printing unit, it is a color chart CT having a plurality of patches each of which is a region of a given color. For example, the sheet feeding unit 1 includes: a reservoir section for reserving a measurement target sheet; an introduction section operable to pick up the measurement target sheet reserved in the reservoir section and introducing the measurement target sheet into the inside of the color measurement device CM, wherein it is constructed, for example, such that it includes a pick-up roller; and a delivery section operable to deliver the measurement target sheet introduced by the introduction section, to the sub-scanning-directionally moving unit 2, wherein it is constructed, for example, such that it includes a conveyance roller.

The sub-scanning-directionally moving unit (sheet conveyance unit) 2 is a sheet conveyance mechanism which is connected to the control processing unit 6 and is operable, according to control of the control processing unit 6, to convey the measurement target sheet delivered from the sheet feeding unit 1, in a sub scanning direction (second direction) orthogonal to a first direction preliminarily set as a main scanning direction. The sub-scanning-directionally moving unit 2 is constructed, for example, such that it includes a plurality of sheet conveyance roller assemblies, and a drive section operable to rotationally drive the sheet conveyance roller assemblies. Each of the sheet conveyance roller assemblies is constructed such that it comprises a drive roller which is rotationally driven by the drive section, and a driven roller which is rotationally driven according to rotational driving of the drive roller. More specifically, in the example depicted in FIG. 2, the sub-scanning-directionally moving unit 2 includes three, first to third, sheet conveyance roller assemblies 20-1 to 20-3. The first to third sheet conveyance roller assemblies 20-1 to 20-3 are arranged from the upstream side (the side of the sheet feeding unit 1) toward the downstream side (discharge side) along the sub scanning direction. Each of the first to third sheet conveyance roller assemblies 20-1 to 20-3 includes a corresponding one of first to third drive rollers 21-1 to 21-3 and a corresponding one of first to third driven rollers 22-1 to 22-3. A measurement target sheet delivered from the sheet feeding unit 1 is nipped between a pair of the first drive roller 21-1 and the first driven roller 22-1, and the first drive roller 21-1 is rotationally driven in a normal rotation direction (e.g., clockwise direction) by the drive section, so that the measurement target sheet is conveyed from the first sheet conveyance roller assembly 20-1 to the second sheet conveyance roller assembly 20-2. The measurement target sheet conveyed to the second sheet conveyance roller assembly 20-2 is conveyed from the second sheet conveyance roller assembly 20-2 to the third sheet conveyance roller assembly 20-3 by the second sheet conveyance roller assembly 20-2, in the same manner as above. Then, the measurement target sheet conveyed to the third sheet conveyance roller assembly 20-3 is conveyed from the third sheet conveyance roller assembly 20-3 to the downstream side by the third sheet conveyance roller assembly 20-3, in the same manner as above.

Although the sub-scanning-directionally moving unit 2 is configured to convey a measurement target sheet in a forward feeding mode from the upstream side toward the downstream side, it may be configured to further convey the measurement target sheet in a backward feeding mode from the downstream side toward the upstream side. In this backward feeding mode, each of the first to third drive rollers 21-1 to 21-3 is rotationally driven in a reverse rotation direction (in the above example, counterclockwise direction) by the drive section, so that the measurement target sheet is conveyed from the downstream side toward the upstream side.

The color measuring unit 3 is a device which is connected to the control processing unit 6 and is operable, according to control of the control processing unit 6, to measure a color of a measurement target. For example, the color measuring unit 3 may be a color measurement sensor operable to acquire given optical information about a measurement target so as to derive a color of the measurement target. In one example, the color measuring unit 3 is a spectrophotometric colorimeter which is equipped with a spectroscopic optical element and a photoelectric conversion element for measuring a reflectance (or transmittance) at each wavelength, and is operable to measure a color of an object based on the reflectance (or transmittance) at each wavelength. In another example, the color measuring unit 3 is a tristimulus value-type colorimeter which is equipped with an optical filter and a photoelectric conversion element for measuring tristimulus values of R, G and B components, and is operable to measure a color of an object based on a color difference between the tristimulus values. The color measuring unit 3 can be calibrated by a white calibration, i.e., by measuring a so-called white calibration plate (reference white plate) capable of reflecting wavelengths in a measurement range at a high reflectance (e.g., about 90% to about 99%).

The main-scanning-directionally moving unit 4 is a moving mechanism which is connected to the control processing unit 6 and is operable, according to control of the control processing unit 6, to move the color measuring unit 3 in the main scanning direction (first direction). The main-scanning-directionally moving unit 4 is constructed, for example, such that it includes: a guide member for guiding the color measuring unit 3; a feed mechanism, such as a rack and pinion assembly (rack-and-pinion) or a feed screw, operable to move the color measuring unit 3 while being guided by the guide member; and a feed mechanism drive section, such as a stepping motor, operable to drive the feed mechanism. In one example, as depicted in FIG. 3, the main-scanning-directionally moving unit 4 is equipped with a rack 31 prepared by cutting teeth on a flat plate-shaped rod and disposed to extend along the main scanning direction, and a pinion (not depicted) which is provided in the color measuring unit 3 and is rotationally driven, for example, by a stepping motor, wherein the pinion and the rack 31 are brought into mesh engagement with each other. When the pinion is rotationally driven by the stepping motor, the color measuring unit 3 is moved in the main scanning direction along the rack 31.

The following description will be made on the assumption that the main scanning direction (first direction) is defined as an x-direction (horizontal direction), wherein a coordinate axis set along the x-direction is defined as an x-axis, and the sub scanning direction (second direction) is defined as a y-direction (vertical direction), wherein a coordinate axis set along the y-direction is defined as a y-axis. These terms will hereinafter be used appropriately.

The imaging unit 5 is a device which is connected to the control processing unit 6 and is operable, according to control of the control processing unit 6, to take an optical image of an object. The imaging unit 5 is constructed, for example, such that it comprises a line sensor (linear image sensor) having a plurality of photoelectric conversion elements arranged along one direction. As depicted in FIG. 3, it is disposed to extend, along the main scanning direction (x-direction), i.e., in a state in which the one direction as an arrangement direction of the plurality of photoelectric conversion elements is coincident with the main scanning direction (x-direction).

As depicted in FIG. 2, the imaging unit 5 is disposed between the first sheet conveyance roller assembly 20-1 and the second sheet conveyance roller assembly 20-2, and the color measuring unit 3 and the main-scanning-directionally moving unit 4 are disposed to allow the color measuring unit 3 to be moved between the second sheet conveyance roller assembly 20-2 and the third sheet conveyance roller assembly 20-3, along the main scanning direction. The imaging unit 5 is operable to image a measurement target sheet with respect to each line along the main scanning direction (x-direction), in a state in which the measurement target sheet is being conveyed in the sub scanning direction (y-direction) by the sub-scanning-directionally moving unit 2, to thereby generate an image (image data) of the measurement target sheet. A relative position y between a measurement target sheet and the color measuring unit 3 in the sub scanning direction can be changed by conveying the measurement target sheet in the sub scanning direction (y-direction) by the sub-scanning-directionally moving unit 2, and a relative position x between the measurement target sheet and the color measuring unit 3 in the main scanning direction can be changed by moving the color measuring unit 3 itself in the main scanning direction (x-direction) by the main-scanning-directionally moving unit 4. In this way, the color measuring unit 3 can be moved to an arbitrary position (x, y) on the measurement target sheet to measure a color at the position (x, y).

The input unit 7 is a device which is connected to the control processing unit 6 and is operable to allow various commands such as a command directing a color measurement of a measurement target, and various data, such as an identifier of a measurement target, necessary for a color measurement, to be input into the color measurement device CM therethrough. For example, it may be a plurality of input switches each assigned with a given function. The output unit 8 is a device which is connected to the control processing unit 6 and is operable, according to control of the control processing unit 6, to output the command and data input through the input unit 7, and a color of a measurement target measured by the color measurement device CM. For example, it may be a display unit such as a CRT display, an LCD or an organic EL display, or a printing unit such as printer.

The input unit 7 and the output unit 8 may be constructed as a touch panel. In the case of constructing such a touch panel, the input unit 7 is a position input unit, such as a resistive type or a capacitive type, operable to detect and accept an operated position, and the output unit 8 is be a display unit. In this touch panel, the position input unit is provided on a display surface of the display unit. When one or more candidates for input content inputtable into the display unit are displayed on the display unit, and a user touches a position of the display surface at which an input content the user wants to input is displayed, the touched position is detected by the position input unit, and the content displayed at the detected position is input into the color measurement device CM, as an input content operated by the user. Such a touch panel allows a user to intuitively understand an input operation, so that it is possible to provide a color measurement device CM which is easy to handle for a user.

The IF unit 9 is a circuit which is connected to the control processing unit 6 and is operable, according to control of the control processing unit 6, to perform input and output of data with respect to an external device. For example, it is may be: an interface circuit conforming to the serial communication standard RS-232C; an interface circuit conforming to the Bluetooth (trademark) standard; an interface circuit for infrared communication conforming to the IrDA (Infrared Data Association) standard or the like; and an interface circuit conforming to the USB (Universal Serial Bus) standard.

The storage unit 10 is a circuit which is connected to the control processing unit 6 and is operable, according to control of the control processing unit 6, to store therein various given programs and various given data. Examples of the various given programs include control processing programs such as a color measurement program for measuring a color of a measurement target, and a position detection program for, in the case where the measurement target is a color chart CT, detecting a position on the color chart CT. For example, the storage unit 10 includes: an ROM (Read Only Memory) as a non-volatile storage element, and an EEPROM (Electrically Erasable Programmable Read Only Memory) as a rewritable non-volatile storage element. The storage unit 10 also includes an RAM (Random Access Memory) operable to store data generated during execution of the given program, or the like, to serve as a so-called "working memory" for the control processing unit 6.

The control processing unit 6 is a circuit which respectively controls the units of the color measurement device CM depending on the functions of the units to derive a color of a measurement target. The control processing unit 6 is constructed, for example, such that it includes a CPU (Central Processing Unit) and its peripheral circuit. During execution of the control processing program and the position detection program, the control processing unit 6 is functionally comprised of a control section 61, an image acquisition processing section 62, an edge information processing section 63, an edge statistic processing section 64, a patch position processing section 65 and a color measurement processing section 66.

The control section 61 respectively controls the units of the color measurement device CM depending on the functions of the units.

The image acquisition processing section 62 acquires an image of the color chart CT by causing the imaging unit 5 to image the color chart CT.

The edge information processing section 63 derives given information regarding an edge as edge information, based on the image of the color chart CT acquired by the image acquisition processing section 62. Examples of the edge information include: edge lines themselves derived from the image of the color chart CT; intervals between the edge lines (inter-edge line intervals); and intervals between lines each intermediate between adjacent two of the edge lines (inter-intermediate line intervals).

Thus, in one or more embodiments, the edge information processing section 63 is operable: based on the image of the color chart CT acquired by the image acquisition processing section 62, to derive one or more edge lines; and, when the number of the derived edge lines is plural, to derive, as the edge information, one or more intervals between the plurality of derived edge lines. Preferably, the one or more intervals between the edge lines are one or more distances between adjacent ones of the edge lines. In this case, the edge information processing section 63 is operable: based on the image of the color chart CT acquired by the image acquisition processing section 62, to derive one or more edge lines; and, when the number of the derived edge lines is plural, to derive, as the edge information, one or more intervals between adjacent ones of the plurality of derived edge lines.

In one or more embodiments, the edge information processing section 63 is operable: based on the image of the color chart CT acquired by the image acquisition processing section 62, to derive one or more edge lines; when the number of the derived edge lines is plural, to derive one or more lines each intermediate between adjacent two of the plurality of derived edge lines; and, when the number of the derived intermediate lines is plural (when the number of the derived edge lines is three or more), to derive, as the edge information, one or more intervals between the plurality of derived intermediate lines. Preferably, the one or more intervals between the intermediate lines are one or more distances between adjacent ones of the intermediate lines. In this case, the edge information processing section 63 is operable: based on the image of the color chart CT acquired by the image acquisition processing section 62, to derive one or more edge lines; when the number of the derived edge lines is plural, to derive one or more lines each intermediate between adjacent two of the plurality of derived edge lines; and, when the number of the derived intermediate lines is plural (when the number of the derived edge lines is three or more), to derive, as the edge information, one or more intervals between adjacent ones of the plurality of derived intermediate lines.

The edge statistic processing section 64 statistically processes the edge information derived by the edge information processing section 63, to thereby derive a given statistic regarding the edge as an edge statistic. Examples of the edge statistic include a histogram about inter-edge line intervals (inter-edge line interval histogram), and a histogram about inter-intermediate line intervals (inter-intermediate line interval histogram). The inter-edge line interval histogram is a frequency distribution chart of inter-edge line interval zones, wherein the inter-edge line interval zones are defined by classifying a length representing the inter-edge line interval into a plurality of zones in increments of a given width (length), and each of the zones is associated with a frequency of occurrence of inter-edge line interval values falls therewithin. In this frequency distribution chart, the horizontal axis represents the inter-edge line interval zones (classes), and the vertical axis represents the frequency (frequency in each class). The inter-intermediate line interval histogram is a frequency distribution chart of inter-intermediate line interval zones, wherein the inter-intermediate line interval zones are defined by classifying a length representing the inter-intermediate line interval into a plurality of zones in increments of a given width (length), and each of the zones is associated with a frequency of occurrence of inter-intermediate line interval values falling therewithin. In this frequency distribution chart, the horizontal axis represents the inter-intermediate line interval zones (classes), and the vertical axis represents the frequency (frequency in each class). Preferably, the statistic processing includes deriving an average value in each class in a histogram about the edge information. In this case, the edge statistic processing section 64 is operable to derive, as most-credible edge information, an average value in one class having the largest (highest) frequency in the edge information histogram.

Thus, in one or more embodiments, the edge statistic processing section 64 is operable to derive, as the edge statistic, the inter-edge line interval histogram from the intervals between the edge lines derived by the edge information processing section 63. Preferably, in this case, the edge statistic processing section 64 is operable to derive, as a most-credible inter-edge line interval, an average value in one class having the largest (highest) frequency in the inter-edge line interval histogram.

In one or more embodiments, the edge statistic processing section 64 is operable to derive, as the edge statistic, the inter-intermediate line interval histogram from the intervals between the intermediate lines derived by the edge information processing section 63. Preferably, in this case, the edge statistic processing section 64 is operable to derive, as a most-credible inter-intermediate line interval, an average value in one class having the largest (highest) frequency in the inter-intermediate line interval histogram.

The patch position processing section 65 derives respective positions of the plurality of patches in the color chart CT, based on the edge information derived by the edge information processing section 63 and the edge statistic derived by the edge statistic processing section 64. Preferably, the patch position processing section 65 is operable, based on the edge lines derived by the edge information processing section 63 and the inter-edge line interval derived by the edge statistic processing section 64, to derive respective positions of the plurality of patches in the color chart CT. More preferably, the patch position processing section 65 is operable, based on the edge lines and the intermediate lines each derived by the edge information processing section 63 and the inter-edge line interval and the inter-intermediate line interval each derived by the edge statistic processing section 64, to derive respective positions of the plurality of patches in the color chart CT. Further preferably, in the above cases, the patch position processing section 65 is operable, based on the inter-edge line interval derived by the edge statistic processing section 64, to determine whether or not the derived edge lines are proper. More specifically, the patch position processing section 65 is operable to interpolate any undetected edge line, based on the inter-edge line interval derived by the edge statistic processing section 64, or remove any erroneously-detected edge line, based on the inter-edge line interval derived by the edge statistic processing section 64. Alternatively, further preferably, in the above cases, the patch position processing section 65 is operable, based on the inter-intermediate line interval derived by the edge statistic processing section 64, to determine whether or not the derived intermediate lines are proper. More specifically, the patch position processing section 65 is operable to interpolate any undetected intermediate line, based on the inter-intermediate line interval derived by the edge statistic processing section 64, or remove any erroneously-detected intermediate line, based on the inter-intermediate line interval derived by the edge statistic processing section 64.

The color measurement processing section 66 causes the color measuring unit 3 to measure respective colors of the plurality of patches, at the respective positions of the plurality of patches derived by the patch position processing section 65.

Figure 5:
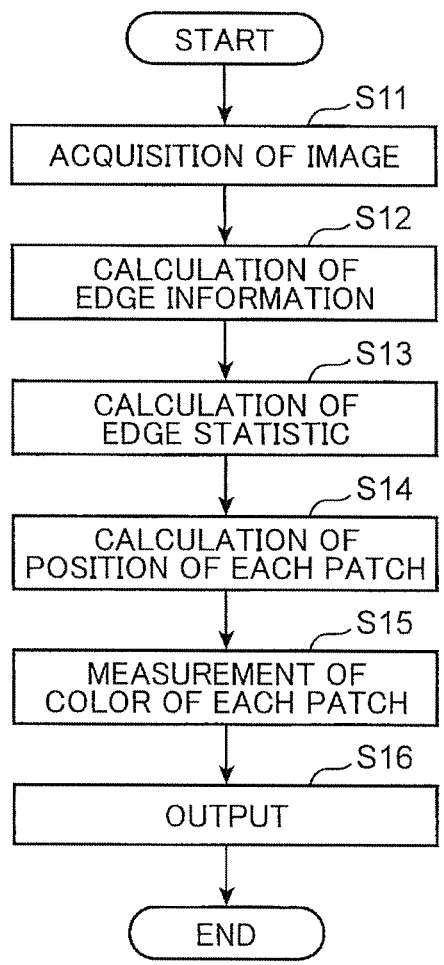
FIG. 5 is a flow chart depicting an operation of the color measurement device in accordance with one or more embodiments of the invention.

Next, an operation of the color measurement device in accordance with one or more embodiments will be described. FIG. 5 is a flow chart depicting the operation of the color measurement device in accordance with one or more embodiments.

In FIG. 5, when a color chart CT is placed in the sheet feeding unit 1 and then start of color measurement is instructed through the input unit 7, the color measurement device CM acquires an image of the color chart CT (S11). More specifically, the image acquisition processing section 62 of the control processing unit 6 operates to acquire the image of the color chart CT by causing the sub-scanning-directionally moving unit 2 to convey the color chart CT from one edge to the other edge of a patch region of the color chart CT in the sub scanning direction (y-direction), and, causing the imaging unit 5 to image, in synchronization with this sub-scanning-directional conveyance, the color chart CT with respect to each line along the main scanning direction (x-direction). The patch region means a region of the color chart CT in which the plurality of patches are located. This patch region is given from the input unit 7, or preliminarily derived by a heretofore-known commonplace means and set in the color measurement device CM.

Subsequently, the color measurement device CM derives edge information based on the image of the color chart CT acquired by the image acquisition processing section 62 (S12).

More specifically, in the case of deriving edge lines, the edge information processing section 63 of the control processing unit 6 operates to firstly subject the image of the color chart CT acquired in the processing S11 to edge extraction using a given edge filter and then to binarization, to thereby generate image data about a binarized edge image (binarized edge image data).

More specifically, the edge information processing section 63 operates in the following manner to, based on the image of the color chart CT, generate image data of an binarized vertical edge image (binarized vertical edge image data) obtained by expressing, as binary values, an edge (edge component) along the vertical direction (y-direction), and image data of an binarized horizontal edge image (binarized horizontal edge image data) obtained by expressing, as binary values, an edge along the horizontal direction (x-direction).

In the case of deriving a vertical edge as an edge along the sub scanning direction (vertical direction, y-direction), it is possible to use, as an example of the edge filter, a difference filter expressed in the following formula (1) which has a number N of difference interval points and is operable to provide a difference output in the main scanning direction (horizontal direction, x-direction).

$$DiffFilterX = [\underbrace{1 \quad 0 \quad ... \quad 0 \quad -1}_{(N-1)_{POINT}}] \quad (1)$$

An inward region of each patch has the same color and almost no change in color density. On the other hand, a boundary (edge) between adjacent ones of the patches has a large change in color density. Thus, the inward region of each patch has a relatively small difference value, and the patch boundary (edge) has a relatively large difference value.

Then, an absolute value of the processing result after the edge filter processing is derived and compared with a preset threshold th1. As a result of this comparison, when the absolute value is equal to or greater than the threshold th1, it is set to 1. On the other hand, when the absolute value is less than the threshold th1, it is set to 0. In this way, respective pixel values of a plurality of pixels along the x-direction are binarized to generate binarized vertical edge image data. Alternatively, noise may be removed after binarization to generate binarized vertical edge image data.

On the other hand, in the case of deriving a horizontal edge as an edge along the main scanning direction (horizontal direction, x-direction), it is possible to use, as an example of the edge filter, a difference filter expressed in the following formula (2) which has a number N of difference interval points and is operable to provide a difference output in the sub scanning direction (vertical direction, y-direction), instead of the above formula (1).

$$DiffFilterY = \left. \begin{bmatrix} 1 \\ 0 \\ \vdots \\ 0 \\ -1 \end{bmatrix} \right\} (N-1)_{POINT} \quad (2)$$

Then, the difference output is processed in the same manner as that in the generation of the binarized vertical edge image data, to generate binarized horizontal edge image data.

Then, the edge information processing section 63 of the control processing unit 6 operates to subject the binarized edge image data of the color chart CT obtained as described above to so-called "straight line detection" based on a Hough transform, to thereby derive edge lines. More specifically, the edge information processing section 63 operates to Hough-transform each of the binarized vertical edge image data and the binarized horizontal edge image data about the color chart CT, to thereby derive vertical edge lines as vertical edge information, and horizontal edge lines as horizontal edge information.

On the other hand, in the case of deriving inter-edge line intervals, the edge information processing section 63 of the control processing unit 6 operates to derive a distance (span) D between adjacent two of the plurality of edge lines derived in the above manner. When the number of the edge lines is three or more, the inter-edge line interval D is derived with respect to each inter-edge line region. Thus, an inter-edge line interval D (k) is derived plurally, correspondingly to two or more inter-edge line regions (k=1 to K1, where K1 is the number of regions between successfully-detected edge lines). More specifically, an inter-vertical edge line interval Dv (kv) is derived from vertical edge lines as the vertical edge information, and an inter-horizontal edge line interval Dh (kh) is derived from horizontal edge lines as the horizontal edge information (kv=1 to Kv1, where Kv1 is the number of regions between successfully-detected vertical edge lines; and kh=1 to Kh1, where Kh1 is the number of regions between successfully-detected horizontal edge lines).

Subsequently, the color measurement device CM statistically processes the edge information derived by the edge information processing section 63, to thereby derive an edge statistic (S13).

More specifically, an inter-edge line interval histogram is derived. The edge statistic processing section 64 of the control processing unit 6 operates to sort, into the inter-edge line interval zones, the inter-edge line intervals D (k) derived as the edge information by the edge information processing section 63, and add the number of inter-edge line intervals D (k) sorted out into each of the inter-edge line interval zone, with respect to each inter-edge line interval zones (each class) to thereby derive a frequency in each of the inter-edge line interval zones, to create a histogram. Preferably, in this case, the edge statistic processing section 64 operates to derive, as the most-credible inter-edge line interval D0, an average value in one class having the largest (highest) frequency in the inter-edge line interval histogram. More specifically, a histogram about inter-vertical edge line intervals (inter-vertical edge line interval histogram) is derived from the inter-vertical edge line intervals Dv (kv), as a vertical edge statistic, and a most-credible inter-vertical edge line interval Dv0 is derived from the inter-vertical edge line interval histogram. Further, a histogram about inter-horizontal edge line intervals (inter-horizontal edge line interval histogram) is derived from the inter-horizontal edge line intervals Dh (kh), as a horizontal edge statistic, and a most-credible inter-horizontal edge line interval Dh0 is derived from the inter-horizontal edge line interval histogram.

In this case, as necessary, the patch position processing section 65 operates to determine, based on the edge statistic derived in the processing S13, whether or not the edge information derived in the processing S12 is proper. More specifically, the patch position processing section 65 operates to determine, based on the most-credible inter-edge line interval D0 derived in the processing S13, whether the edge lines derived in the processing S12 are proper. Further preferably, the patch position processing section 65 operates to determine, based on the most-credible inter-vertical edge line interval Dv0 derived in the processing S13, whether or not the vertical edge lines derived in the processing S12 are proper. The patch position processing section 65 also operates to determine, based on the most-credible inter-horizontal edge line interval Dh0 derived in the processing S13, whether or not the horizontal edge lines derived in the processing S12 are proper.

On the other hand, in the case of deriving inter-intermediate line intervals, the edge information processing section 63 of the control processing unit 6 operates to derive a plurality of intermediate lines between adjacent ones of the edge lines derived in the above manner, and derive a distance (span) L between adjacent two of the plurality of derived intermediate lines. When the number of the intermediate lines is three or more, the inter-intermediate line interval is derived with respect to each inter-intermediate line region. Thus, an inter-intermediate line interval L (m) is derived plurally, correspondingly to two or more inter-intermediate line regions (m=1 to M1, where M1 is the number of regions between successfully-detected edge lines). More specifically, vertical intermediate lines which are lines each intermediate between adjacent two of the plurality of vertical edge lines (intermediate lines between the vertical edge lines) are derived from the plurality of vertical edge lines, and an inter-vertical intermediate line interval Lv (my) is derived from the vertical intermediate lines as the vertical edge information. Further, horizontal intermediate lines which are lines each intermediate between adjacent two of the plurality of horizontal edge lines (intermediate lines between the horizontal edge lines) are derived from the plurality of horizontal edge lines, and an inter-horizontal intermediate line interval Lh (mh) is derived from the horizontal intermediate lines as the horizontal edge information (mv=1 to Mv1, where Mv1 is the number of regions between intermediate lines based on successfully-detected vertical edge lines; and mh=1 to Mh1, where Mh1 is the number of regions between intermediate lines based on successfully-detected horizontal edge lines).

Then, in the case of deriving an inter-intermediate line interval histogram, the edge statistic processing section 64 of the control processing unit 6 operates to sort, into a plurality of inter-intermediate line interval zones, the inter-intermediate line intervals L (m) derived as the edge information by the edge information processing section 63, and add the number of inter-intermediate line intervals L (m) sorted out into each of the inter-intermediate line interval zones, with respect to each inter-intermediate line interval zone (each class) to thereby derive a frequency in each of the inter-intermediate line interval zones, to create a histogram. Preferably, in this case, the edge statistic processing section 64 operates to derive, as the most-credible inter-intermediate line interval L0, an average value in one class having the largest (highest) frequency in the inter-intermediate line interval histogram. More specifically, a histogram about inter-vertical intermediate line intervals (inter-vertical intermediate line interval histogram) is derived from the inter-vertical intermediate line intervals Lv (mv), as the vertical edge statistic, and a most-credible inter-vertical intermediate line interval Lv0 is derived from the inter-vertical intemiediate line interval histogram. Further, a histogram about inter-horizontal intermediate line intervals (inter-horizontal intermediate line interval histogram) is derived from the inter-horizontal intermediate line intervals Lh (mh), as the horizontal edge statistic, and a most-credible inter-horizontal intermediate line interval Lh0 is derived from the inter-horizontal intermediate line interval histogram.

Subsequently, the color measurement device CM derives respective positions of the plurality of patches in the color chart CT, based on the edge information derived in the processing S12 and the edge statistic derived in the processing S13 (S14). More specifically, the patch position processing section 65 firstly operates to derive vertical intermediate lines based on the vertical edge information and the vertical statistic. Then, the patch position processing section 65 operates to derive horizontal intermediate lines based on the horizontal edge information and the horizontal statistic.

The patch position processing section 65 operates to determine, based on the most-credible inter-intermediate line interval L0 derived in the processing S13, whether or not the intermediate lines determined in the processing S12 are proper, and interpolate any undetected intermediate line, based on a result of the determination. More specifically, the patch position processing section 65 operates to determine, based on the most-credible inter-vertical intermediate line interval Lv0 derived in the processing S13, whether or not the vertical intermediate lines determined in the processing S12 are proper, and interpolate any undetected vertical intermediate line, based on a result of the determination. The patch position processing section 65 also operates to determine, based on the most-credible inter-horizontal intermediate line interval Lh0 derived in the processing S13, whether or not the horizontal intermediate lines determined in the processing S12 are proper, and interpolate any undetected horizontal intermediate line, based on a result of the determination.

Then, the patch position processing section 65 operates to derive intersection points of the plurality of vertical intermediate lines and the plurality of horizontal intermediate lines derived in the above manner, as respective positions (x, y) of the patches.

Subsequently, based on the color measurement processing section 66 of the control processing unit 6, the color measurement device CM moves the color measuring unit 3 to each of the positions (x, y) derived in the processing S14 to allow the color measuring unit 3 to measure a color of each patch (S15).

Subsequently, upon completion of the measurement of colors of the patches, the color measurement device CM outputs the colors of the patches measured in the processing S15 to the output unit 8 (S16) to complete the processing routine. As needed, the control section 61 of the control processing unit 6 may operate to output the colors of the patches measured in the processing S15 to the IF unit 9.

Figure 6:
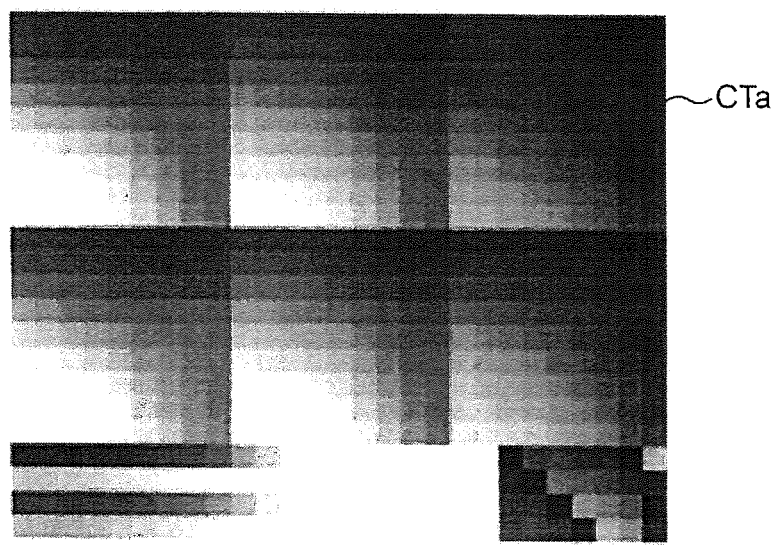
FIG. 6 is a diagram depicting, as one example, an image of a color chart of a first type.
Figure 7:
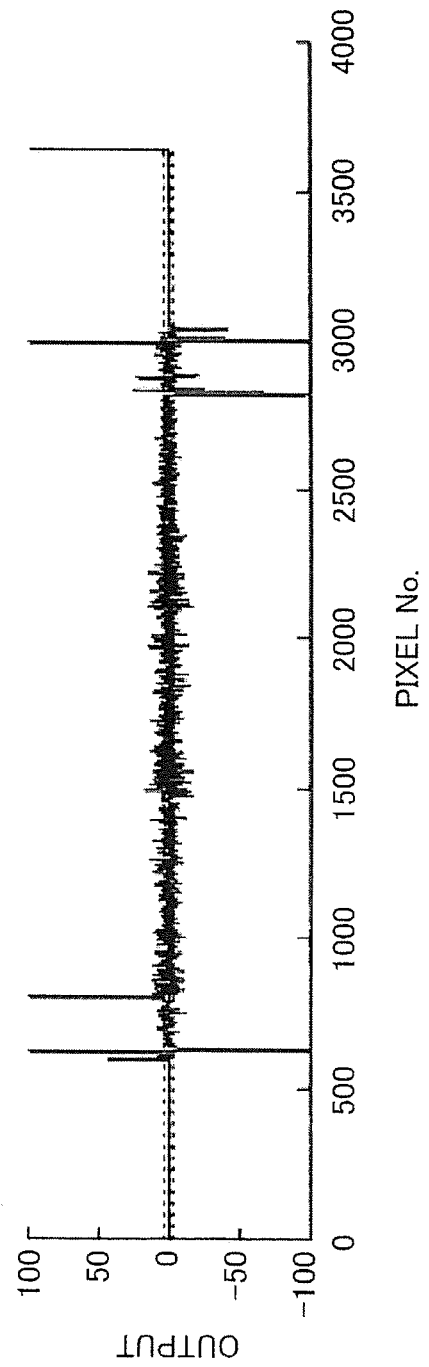
FIG. 7 is a chart depicting one example of a result of processing for the color chart depicted in FIG. 6, wherein an image at a certain y-directional position was subjected to processing using a difference filter having a number N of difference interval points along a horizontal direction.
Figure 8:
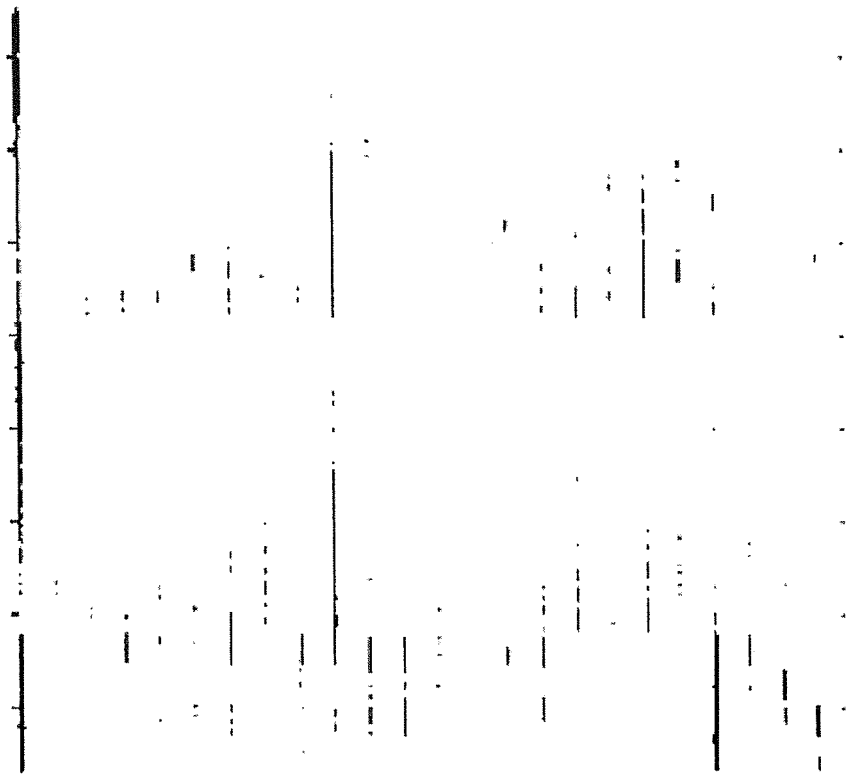
FIG. 8 is a diagram depicting, as one example, a binarized vertical edge image of the color chart depicted in FIG. 6.
Figure 9:
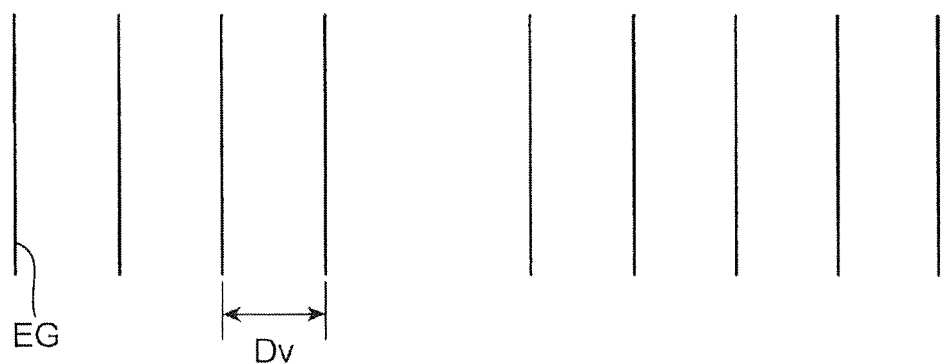
FIG. 9 is a diagram depicting, as one example, vertical edge lines of the color chart depicted in FIG. 6.
Figure 10:
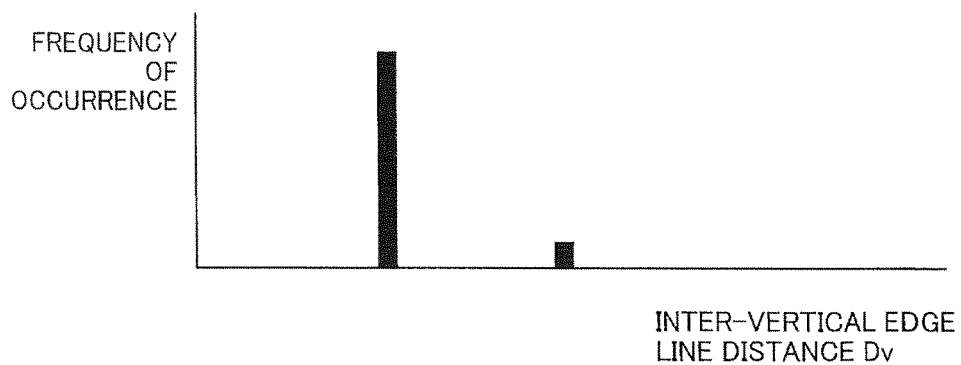
FIG. 10 is a diagram depicting, as one example, a histogram about inter-vertical edge line intervals in the color chart depicted in FIG. 6.
Figure 11:
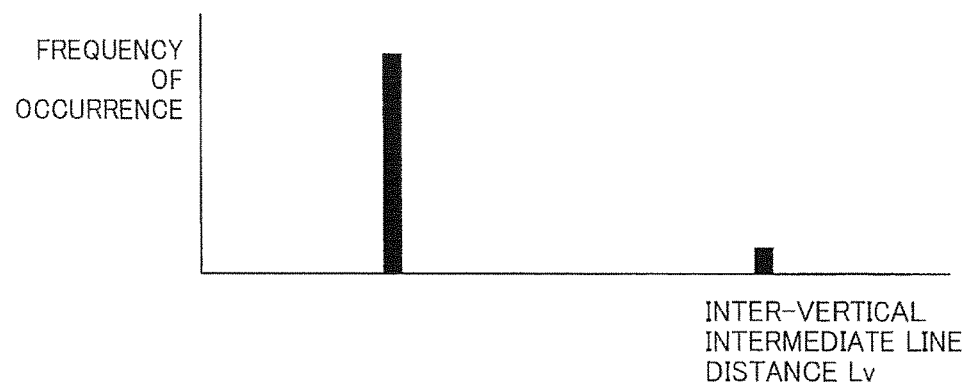
FIG. 11 is a diagram depicting, as one example, a histogram about inter-vertical intermediate line intervals in the color chart depicted in FIG. 6.
Figure 12A:
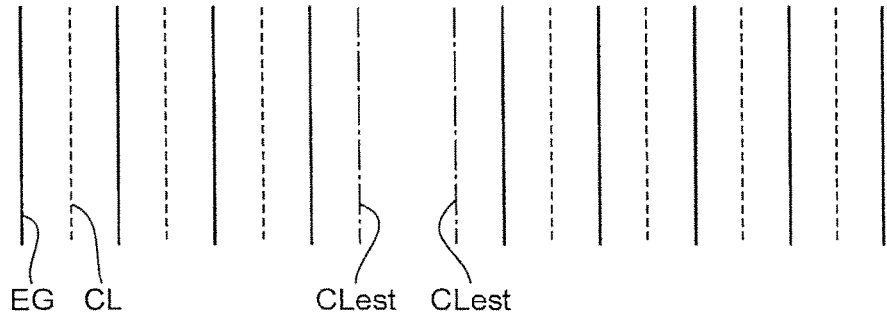
FIG. 12A is a first diagram for explaining, as one example, the vertical edge lines and vertical intermediate lines in the color chart depicted in FIG. 6.
Figure 12B:
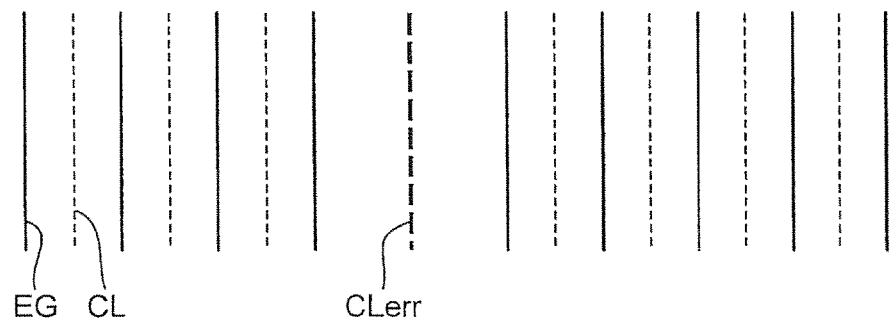
FIG. 12B is a second diagram for explaining, as one example, the vertical edge lines and vertical inteiniediate lines in the color chart depicted in FIG. 6.
Figure 12C:
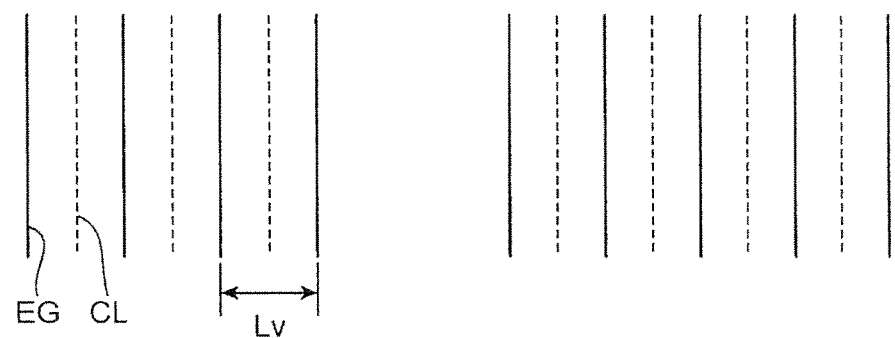
FIG. 12C is a third diagram for explaining, as one example, the vertical edge lines and vertical intermediate lines in the color chart depicted in FIG. 6.
Figure 13:
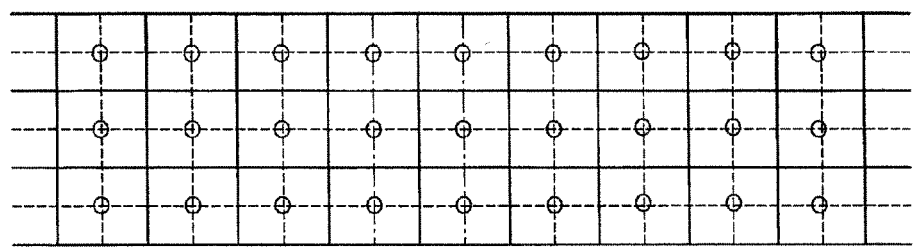
FIG. 13 is a diagram depicting, as one example, an actual measured position (○) of each patch in the color chart depicted in FIG. 6.
Figure 14A:
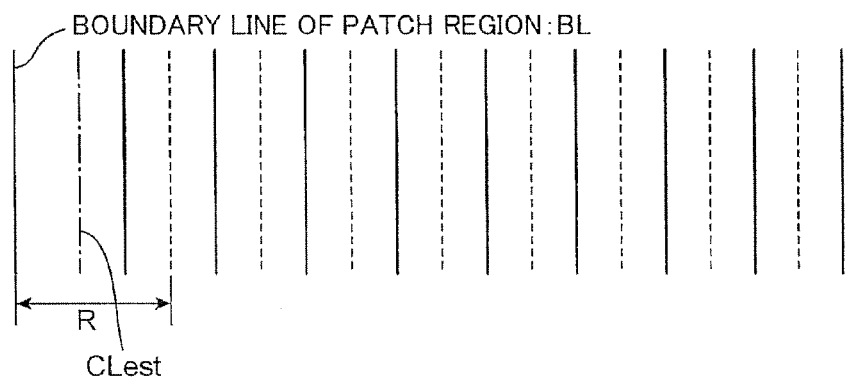
FIG. 14A is a first diagram for explaining, as one example, the vertical edge lines and the vertical intermediate lines, in the case where an endmost one of the vertical edge lines is not derived as the vertical edge line.
Figure 14B:
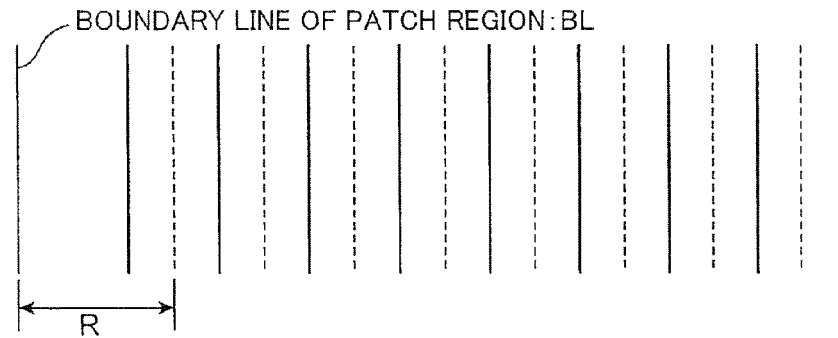
FIG. 14B is a second diagram for explaining, as one example, the vertical edge lines and the vertical intermediate lines, in the case where an endmost one of the vertical edge lines is not derived as the vertical edge line.
Figure 15:
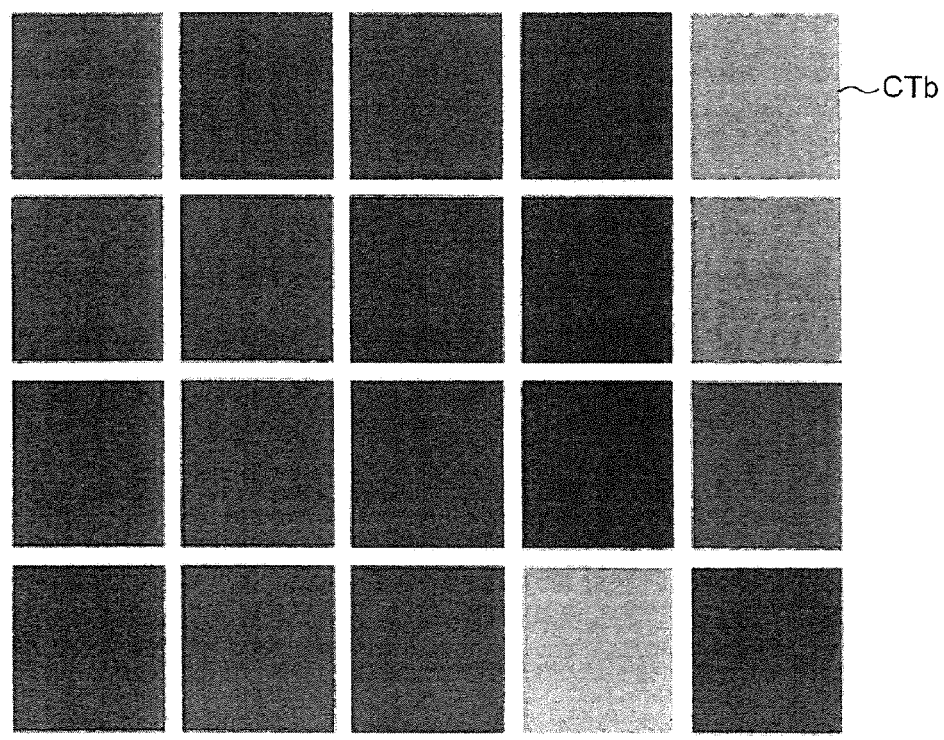
FIG. 15 is a diagram depicting, as one example, an image of a color chart of a second type.
Figure 16:
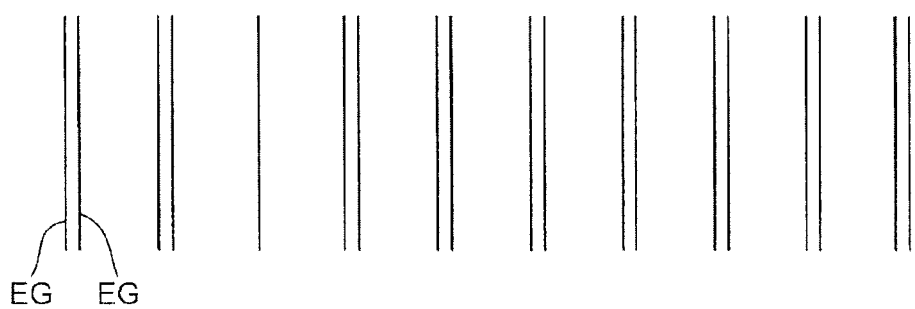
FIG. 16 is a diagram depicting, as one example, vertical edge lines of the color chart depicted in FIG. 15.
Figure 17:
FIG. 17 is a diagram depicting, as one example, a histogram about inter-vertical edge line intervals in the color chart depicted in FIG. 15.
Figure 18A:
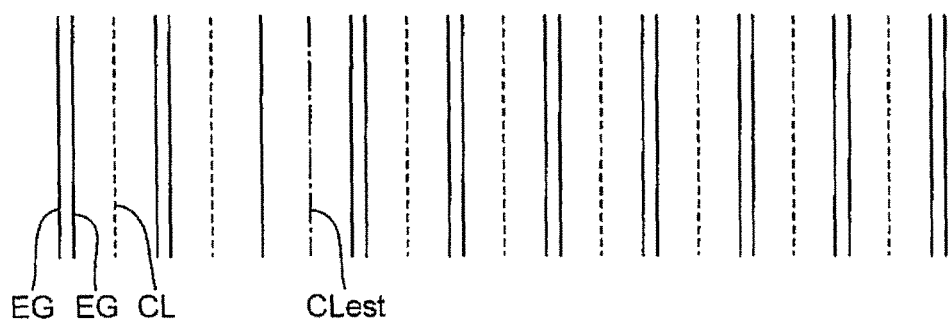
FIG. 18A is a first diagram for explaining, as one example, the vertical edge lines and intermediate lines in the color chart depicted in FIG. 15.
Figure 18B:
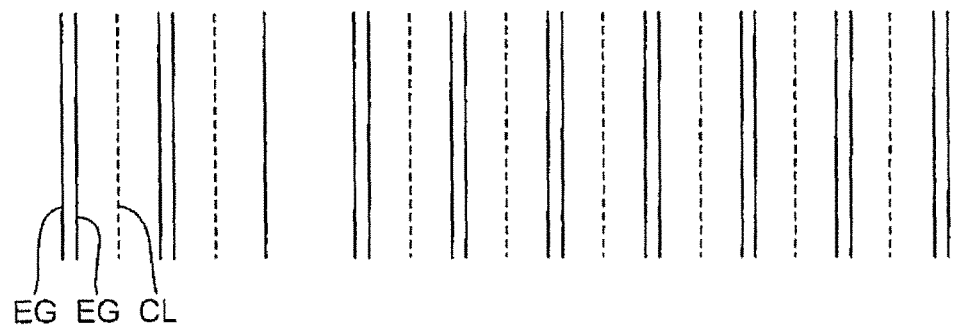
FIG. 18B is a second diagram for explaining, as one example, the vertical edge lines and intermediate lines in the color chart depicted in FIG. 15.
Figure 19:
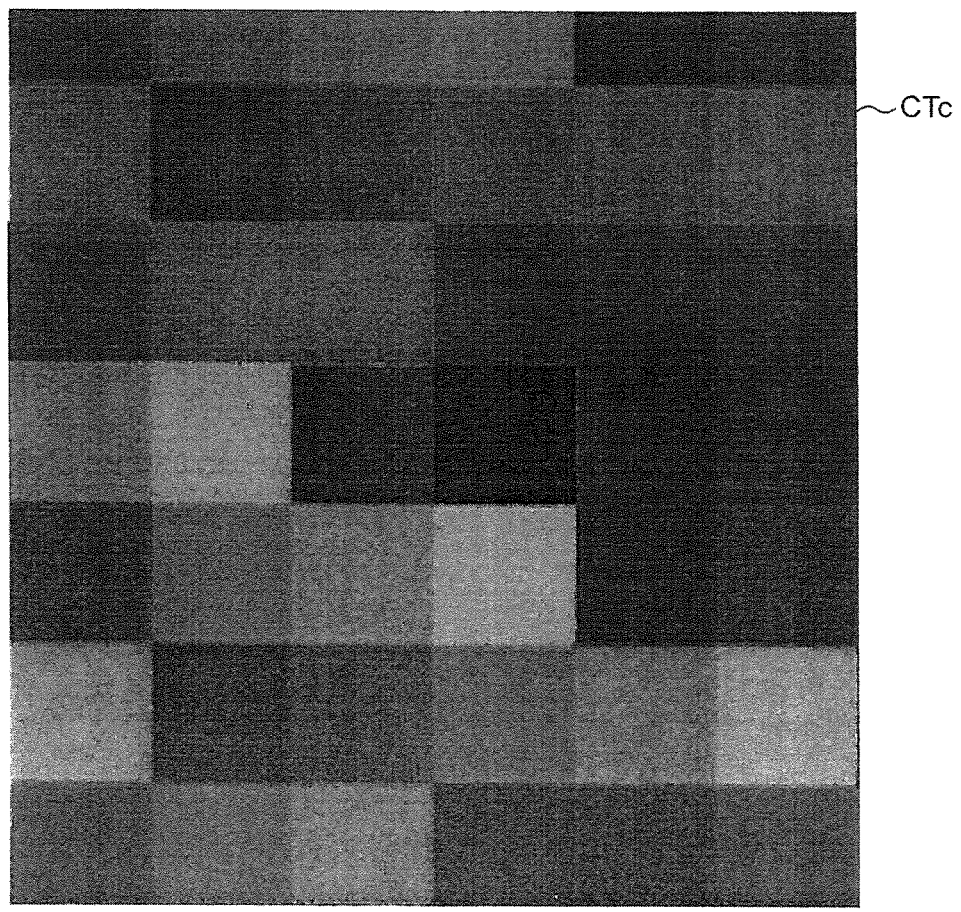
FIG. 19 is a diagram depicting, as one example, an image of a color chart of a third type.
Figure 20:
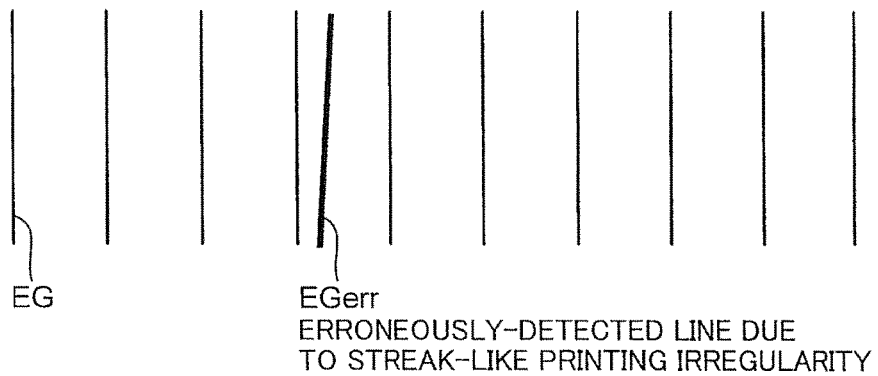
FIG. 20 is a diagram depicting, as one example, vertical edge lines of the color chart depicted in FIG. 19.
Figure 21:
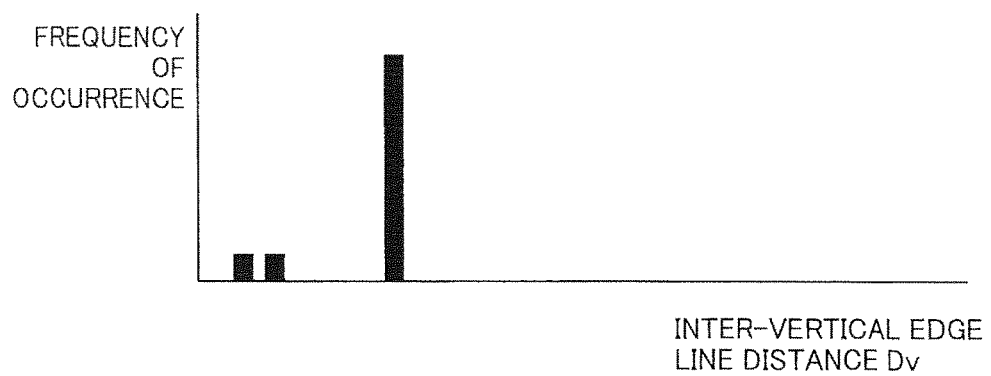
FIG. 21 is a diagram depicting, as one example, a histogram about inter-vertical edge line intervals in the color chart depicted in FIG. 19.
Figure 22A:
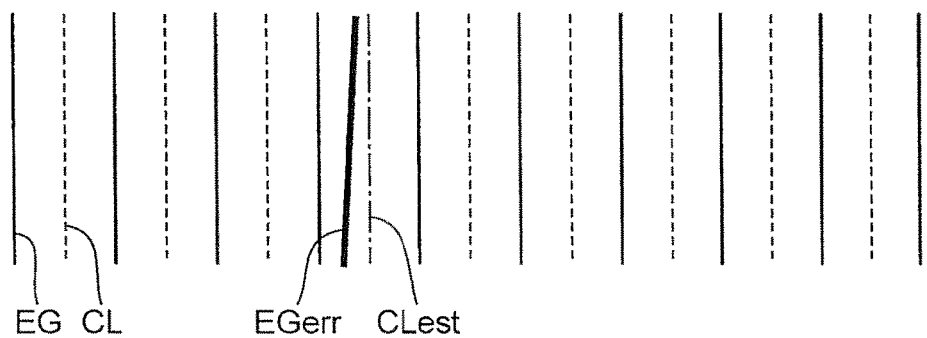
FIG. 22A is a first diagram for explaining, as one example, the vertical edge lines and intermediate lines in the color chart depicted in FIG. 19.
Figure 22B:
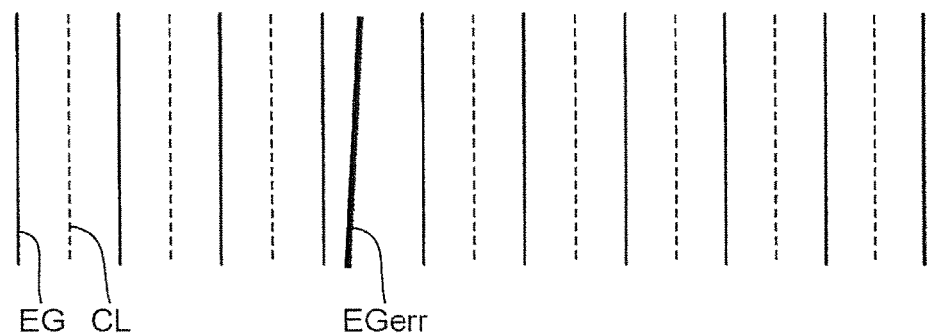
FIG. 22B is a second diagram for explaining, as one example, the vertical edge lines and intermediate lines in the color chart depicted in FIG. 19.

Next, the above operation will be more specifically described by showing a color chart CT as an example. FIG. 6 is a diagram depicting, as one example, an image of a color chart of a first type. FIG. 7 is a chart depicting one example of a result of processing for the color chart depicted in FIG. 6, wherein an image at a certain y-directional position was subjected to processing using a difference filter having a number N of difference interval points along the horizontal direction. In FIG. 7, the horizontal axis represents a pixel number (i.e., a position in the horizontal direction x) in the imaging unit 5, and the vertical axis represents a difference value. FIG. 8 is a diagram depicting, as one example, a binarized vertical edge image of the color chart depicted in FIG. 6. FIG. 9 is a diagram depicting, as one example, vertical edge lines of the color chart depicted in FIG. 6. FIG. 10 is a diagram depicting, as one example, a histogram about inter-vertical edge line intervals in the color chart depicted in FIG. 6. In FIG. 10, the horizontal axis represents each inter-edge line interval zone as each class, and the vertical axis represents a frequency in each class. FIG. 11 is a diagram depicting, as one example, a histogram about inter-vertical intermediate line intervals in the color chart depicted in FIG. 6. In FIG. 11, the horizontal axis represents each inter-intermediate line interval zone as each class, and the vertical axis represents a frequency in each class. FIG. 12 is a diagram for explaining, as one example, the vertical edge lines and intermediate lines in the color chart depicted in FIG. 6. FIG. 12A depicts intermediate lines derived based on the vertical edge lines, the inter-vertical edge line interval histogram and the inter-vertical intermediate line interval histogram. FIG. 12B depicts intermediate lines derived based only on the vertical edge lines, and FIG. 12C depicts intermediate lines derived based on the vertical edge lines and the inter-vertical edge line interval histogram. FIG. 13 is a diagram depicting, as one example, an actual measured position (○) of each patch in the color chart depicted in FIG. 6. FIG. 14 is a diagram for explaining, as one example, the vertical edge lines and the vertical intermediate lines, in the case where an endmost one of the vertical edge lines is not derived as the vertical edge line. FIG. 14A depicts intermediate lines derived based on the patch region, the vertical edge lines, the inter-vertical edge line interval histogram and the inter-vertical intermediate line interval histogram, and FIG. 14B depicts intermediate lines derived based only on the vertical edge lines. FIG. 15 is a diagram depicting, as one example, an image of a color chart of a second type. FIG. 16 is a diagram depicting, as one example, vertical edge lines of the color chart depicted in FIG. 15. FIG. 17 is a diagram depicting, as one example, a histogram about inter-vertical edge line intervals in the color chart depicted in FIG. 15. In FIG. 17, the horizontal axis represents each inter-edge line interval zone as each class, and the vertical axis represents a frequency in each class. FIG. 18 is a diagram for explaining, as one example, the vertical edge lines and intermediate lines in the color chart depicted in FIG. 15. FIG. 18A depicts intermediate lines derived based on the vertical edge lines, the inter-vertical edge line interval histogram and the inter-vertical intermediate line interval histogram, and FIG. 18B depicts intermediate lines derived based on the vertical edge lines and the inter-vertical edge line interval histogram. FIG. 19 is a diagram depicting, as one example, an image of a color chart of a third type. FIG. 20 is a diagram depicting, as one example, vertical edge lines of the color chart depicted in FIG. 19. FIG. 21 is a diagram depicting, as one example, a histogram about inter-vertical edge line intervals in the color chart depicted in FIG. 19. In FIG. 21, the horizontal axis represents each inter-edge line interval zone as each class, and the vertical axis represents a frequency in each class. FIG. 22 is a diagram for explaining, as one example, the vertical edge lines and vertical intermediate lines in the color chart depicted in FIG. 19. FIG. 22A depicts intermediate lines derived based on the vertical edge lines, the inter-vertical edge line interval histogram and the inter-vertical intermediate line interval histogram, and FIG. 22B depicts intermediate lines derived based on the vertical edge lines and the inter-vertical edge line interval histogram.

First of all, as one example, an operation in the case of a color chart CTa of the first type depicted in FIG. 6 will be described. In FIG. 5, the image acquisition processing section 62 operates to acquire an image of the color chart CTa of the first type as depicted in FIG. 6, in the processing S11. The color chart CTa of the first type depicted in FIG. 6 is constructed such that it comprises a plurality of patches arranged to allow colors of the patches to form a gradation.

Subsequently, in the processing S12, the edge information processing section 63 operates to derive the edge information. In this example, vertical edge lines and horizontal edge lines are derived, and vertical intermediate lines and horizontal intermediate lines are derived, respectively, from the actually derived vertical edge lines and the actually derived horizontal edge lines. Further, inter-vertical edge line intervals Dv (kv) and inter-horizontal edge line interval Dh (kh) are derived, respectively, from the actually derived vertical edge lines and the actually derived horizontal edge lines, and inter-vertical intermediate line interval Lv (mv) and inter-horizontal intermediate line interval Lh (mh) are derived, respectively, from the actually derived vertical intermediate lines and the actually derived horizontal intermediate lines.

Here, the aforementioned edge filters are used for edge detection. In the case of the color chart CTa including a gradation as depicted in FIG. 6, a low contrast region can occur in a boundary between adjacent patches, leading to difficulty in detecting edges by edge detection based on the difference schemes expressed in the formulas 1 and 2, as depicted in FIGS. 7 and 8. FIG. 7 depicts one example of a result of processing for the color chart CTa depicted in FIG. 6, wherein an image at a certain y-directional position was subjected to processing using a difference filter having a number N of difference interval points along the x-direction. FIG. 8 depicts a binarized vertical edge image obtained by subjecting the color chart CTa depicted in FIG. 6 to edge extraction using the edge filter expressed in the formula (1) and binarizing resulting extracted edges. When data about the binarized vertical edge image of the color chart CTa depicted in FIG. 8, i.e., binarized vertical edge image data pict Ver 0 (x, y), is subjected to a Hough transform, vertical edge lines depicted, for example, in FIG. 9, are derived. Assume that there is a region having difficulty in detecting edges, as mentioned above. In this case, even though a 5th edge line EG5 counted from a left endmost vertical edge line on the drawing sheet originally exists in the actual color chart CTa, the 5th edge line EG5 counted from the left endmost vertical edge line on the drawing sheet is not detected as a result of the Hough transform, and thereby disappears from the result as depicted in FIG. 9.

When one originally-existing edge line EG is not detected, and intermediate lines CL between the edge lines EG are derived so as to derive respective positions of the patches, an erroneous intermediate line CLerr is undesirably derived in a region around the originally-existing edge line EG. In the example depicted in FIG. 9, when the originally-existing 5th edge line EG is not detected, and intermediate lines CL between the edge lines EG are derived so as to derive respective positions of the patches, an erroneous intermediate line CLerr is undesirably derived in a region around the originally-existing 5th edge line EG5. Although the above description has been made with regard to the vertical edge lines, a similar operation is performed for horizontal edge lines. Further, although the following description will be made with regard to the vertical edge lines, a similar operation is performed for horizontal edge lines.

For this reason, in one or more embodiments, the edge statistic processing section 64 operates to derive an edge statistic, in the processing S13. In this example, an inter-vertical edge line interval histogram and an inter-horizontal edge line interval histogram.

For example, as a result of deriving inter-vertical edge line intervals with respect to the color chart CT depicted in FIG. 6 and deriving a histogram thereabout, an inter-vertical edge line interval histogram depicted in FIG. 10 is derived. The number of properly-detected vertical edge lines is considered to be generally greater than the number of undetected and erroneously-detected vertical edge lines. Thus, the inter-vertical edge line interval zone as a class having the largest frequency is considered to include a most-credible, proper, true value Dv0. Thus, in one or more embodiments, in the processing S13, an average of inter-vertical edge line interval values belonging to the class having the largest frequency is defined as a most-credible inter-vertical edge line interval Dv0, i.e., the true value Dv0. In the example depicted in FIG. 10, the 5th edge line EG5 is undetected in FIG. 9, and therefore a frequency in a class of 2×Dv0 is one.

After the true value (most-credible inter-vertical edge line interval) Dv0 is derived in this manner, in the processing S14, the patch position processing section 65 operates to determine, based on the edge statistic derived in the processing S13, whether or not the edge information derived in the processing S12 is proper. In this example, the patch position processing section 65 operates to determine whether or not a distance between adjacent two of the vertical edge lines is equal to the true inter-vertical edge line interval value Dv0, wherein the patch position processing section 65 operates to, when the distance between the adjacent vertical edge lines is determined to be equal to the true inter-vertical edge line interval value. Dv0, derive an intermediate line between the adjacent vertical edge lines, and, when the distance between the adjacent vertical edge lines is determined to be not equal to the true inter-vertical edge line interval value Dv0, derive no intermediate line. Thus, vertical edge lines EG and vertical intermediate lines CL depicted in FIG. 12C are obtained.

Here, in the example depicted in FIG. 12C, the 5th vertical edge line is undetected, and thereby a vertical intermediate line normally lying between the 4th and 5th vertical edge lines and a vertical intermediate line normally lying between the 5th and 6th vertical edge lines are undetected. For this reason, in one or more embodiments, in the processing S13, the edge statistic processing section 64 operates to additionally derive the inter-vertical intermediate line interval histogram and the inter-horizontal intermediate line interval histogram, as mentioned above.

For example, as a result of deriving inter-vertical intermediate line intervals with respect to the color chart CT depicted in FIG. 6 and deriving a histogram thereabout, an inter-vertical intermediate line interval histogram depicted in FIG. 11 is derived. As mentioned above, the number of properly-detected vertical edge lines is considered to be generally greater than the number of undetected and erroneously-detected vertical edge lines, so that the number of properly-detected vertical intermediate lines is also considered to be generally greater than the number of undetected and erroneously-detected vertical intermediate lines. Thus, in the inter-vertical intermediate line interval histogram, the inter-vertical intermediate line interval zone as a class having the largest frequency is considered to include a most-credible, proper, true value Lv0. Thus, in one or more embodiments, in the processing S13, an average of inter-vertical intermediate line interval values belonging to the class having the largest frequency is defined as a most-credible inter-vertical intermediate line interval Lv0, i.e., the true value Lv0. In the example depicted in FIG. 11, the 5th edge line EG5 is undetected in FIG. 9, and therefore a frequency in a class of 3× Lv0 is one.

In this example, the patch position processing section 65 operates to determine whether or not a distance between adjacent two of the vertical edge lines is equal to an integral multiple of (N1 times) the true inter-vertical intermediate line interval value Lv0, wherein the patch position processing section 65 operates to, when the distance between the adjacent vertical edge intermediate lines is determined to be equal to one time the true inter-vertical edge line interval value Lv0, determine that an intermediate line between the adjacent vertical edge lines is a proper intermediate line, and, when the distance between the adjacent vertical edge intermediate lines is determined to be an integral multiple of two times or more (N1 times, where N1 is an integer of 2 or more) the true inter-vertical edge intermediate line interval value Lv0, divide a region between the adjacent vertical intermediate lines equally into N sub-regions and interpolate an intermediate line at one or more positions defining the N equally divided sub-regions. For example, in the example illustrated in FIG. 9, two vertical intermediate lines CLest, CLest are interpolated as respective vertical intermediate lines normally lying between the 4th and 5th vertical edge lines and between the 5th and 6th vertical edge lines, as illustrated in FIG. 12A.

After deriving the vertical intermediate lines in the above manner and deriving horizontal intermediate lines in a similar manner, intersection points of the plurality of derived vertical intermediate lines and the plurality of derived horizontal intermediate lines are derived as respective positions (x, y) of the patches. For example, with respect to the color chart CT depicted in FIG. 6, vertical intermediate lines and horizontal intermediate lines are derived as indicated by the broken lines in FIG. 13, and intersection points thereof are derived as respective positions (x, y) of the patches, as indicated by circular marks (○) in FIG. 13.

Then, in the processing S15, a color of each patch is measured at the position of the patch, and a result of the measurement is output in the processing S16.

The above example has been described on the assumption that the 5th vertical edge line counted from the left endmost vertical edge line on the drawing sheet is undetected as depicted in FIG. 9. Alternatively, in the case where a 1st vertical edge line as an endmost (in FIG. 14B, left endmost)

vertical edge line on the drawing sheet) is undetected as depicted in FIG. 14B, the undetected endmost 1st vertical edge line can also be interpolated by the following processing. As mentioned above, the patch region in which the plurality of patches are located is given from the input unit 7, or preliminarily derived by a heretofore-known commonplace means and set in the color measurement device CM.

In this case, in the processing S14, the patch position processing section 65 operates to firstly determine whether or not a distance R between an actually-derived endmost (in FIG. 14B, left endmost) vertical intermediate line on the drawing sheet and a boundary line of the patch region is equal to a value obtained by adding, to an integral multiple of (N2 times) of the true inter-vertical intermediate line interval value Lv0, one-half thereof (Lv0/2). In this determination, a margin of ±α may be taken into account. As a result of this determination, when R=Lv0×N2+Lv0/2 (in the case where a margin of ±α is taken into account, R=Lv0×N2+Lv0/2±α) is satisfied, the patch position processing section 65 operates to extrapolate (interpolate) a vertical intermediate line CLest by a number of N2 at one or more positions away from the actually-derived endmost (in FIG. 14B, left endmost) vertical intermediate line on the drawing sheet at intervals of the true inter-vertical intermediate line interval value Lv0. On the other hand, when R=Lv0×N2+Lv0/2 (in the case where a margin of ±α is taken into account, R=Lv0×N2+Lv0/2+α) is not satisfied, the patch position processing section 65 operates to perform no interpolation of the vertical intermediate line.

For example, in the example depicted in FIG. 14B, the distance R between the actually-derived left endmost vertical intermediate line and the boundary line of the patch region is equal to Lv0×1+Lv0±α, and, through the above processing, one vertical intermediate line CLest is extrapolated (interpolated) at a position away from the actually-derived left endmost vertical inteiniediate line by the true inter-vertical intermediate line interval value Lv0, as depicted in FIG. 14A.

As another example, an operation in the case of a color chart CTb of the second type depicted in FIG. 15 will be described. In the color chart CTa of the first type depicted in FIG. 6, the patches are arranged such that adjacent ones thereof are in contact with each other. Differently, in the color chart CTb of the second type depicted in FIG. 15, a plurality of patches are arranged such that adjacent ones thereof are spaced apart from each other with a given distance therebetween. That is, in the color chart CTb of the second type, there is a gap between adjacent patches.

In the color chart CTb of the second type, edge lines are derived in the same manner as described above. In this case, when there is a relatively large density difference between the gap and each of the patches, edge lines are properly derived, and, specifically, two edge lines are derived with respect to each gap. On the other hand, when the density difference between the gap and each of the patches is relatively low, edge lines are not properly derived, and, specifically, only one edge line is derived with respect to each gap, or no edge line is detected in each gap. FIG. 16 depicts one example where, when vertical edge lines are derived with respect to the color chart CTb of the second type depicted in FIG. 15, only one edge line is derived in a 3rd gap counted from a left endmost gap on the drawing sheet.

Even in this case, through the aforementioned processing, a vertical intermediate line is interpolated to derive respective positions of the patches. More specifically, for example, in the processing S12, the vertical edge lines depicted in FIG. 16 are derived, and, in the processing S13, an inter-vertical edge line interval histogram depicted in FIG. 17 is derived with respect to the vertical edge lines depicted in FIG. 16.

As mentioned above, the number of properly-detected vertical edge lines is considered to be generally greater than the number of undetected and erroneously-detected vertical edge lines. Thus, in the inter-vertical edge line interval histogram, there are two peaks in a class corresponding to a true value DGv0 of a length of the gap (gap length), and a class corresponding to a true value Dv0 of an inter-vertical edge line interval. Therefore, by preliminarily setting, in the color measurement device CM, information about at least one of horizontal lengths of the patch and the gap (e.g., information that the horizontal length of the patch is in the range of 6 mm to 30 mm, and the gap length is 20% or less of the patch length), the patch position processing section 65 can operate to determine a peak in the class corresponding to the true inter-vertical edge line interval value Dv0, and derive the true inter-vertical edge line interval value Dv0. For example, by preliminarily setting information about the horizontal patch length in the color measurement device CM, the patch position processing section 65 can operate to determine that a class having a range within which the preliminarily set horizontal patch length falls and having a peak is the class corresponding to the true inter-vertical edge line interval value Dv0, and derive an average value of horizontal patch length values belonging to the class, as the true inter-vertical edge line interval value Dv0. In FIG. 17, only one edge line can be detected in the 3rd gap counted from the left endmost gap on the drawing sheet, so that a frequency equivalent to a value obtained by adding the gap length to the inter-vertical edge line interval is one.

After the true inter-vertical edge line interval value Dv0 is derived in this manner, the patch position processing section 65 operates to determine proper vertical edge lines, and derive vertical edge intermediate lines from the determined proper vertical edge lines, in the same manner as described above. From an inter-vertical edge intermediate line histogram, a proper inter-vertical edge intermediate line interval Lv0 is determined. It is determined whether or not a distance or interval between adjust two of the vertical edge intermediate lines is equal to the true inter-vertical edge intermediate line interval Lv0, and, when the distance between adjust two of the vertical edge intermediate lines is equal to the true inter-vertical edge intermediate line interval Lv0, the adjacent vertical edge intermediate lines are determined as proper intermediate lines. As necessary, an intermediate line is interpolated. That is, through the above processing, only proper intermediate lines depicted in FIG. 18B are derived from the actually-derived vertical edge lines depicted in FIG. 16, and then, although a 3rd intermediate line counted from a left endmost intermediate line on the drawing sheet is undetected in FIG. 18B, an intermediate line CLest is interpolated at a position of the 3rd intermediate line, as depicted in FIG. 18A.

After deriving the vertical intermediate lines in the above manner and deriving horizontal intermediate lines in a similar manner, intersection points thereof are derived as respective positions (x, y) of the patches. Then, in the processing S15, a color of each patch is measured at the position of the patch, and a result of the measurement is output in the processing S16.

As yet another example, an operation in the case of a color chart CTc of the third type depicted in FIG. 19 will be described. The color chart CTc of the third type depicted in FIG. 19 has a streak-like printing irregularity.

In the color chart CTc of the third type, when edge lines are derived in the above manner, the streak-like printing irregularity is erroneously detected as an edge line. FIG. 20 depicts one example where, when vertical edge lines are derived with respect to the color chart CTc of the third type depicted in FIG. 19, an erroneously-detected edge line EGerr due to the streak-like printing irregularity is located between a 4th vertical edge line EG and a 5th vertical edge line EG counted from a left endmost vertical edge line on the drawing sheet.

Even in this case, through the aforementioned processing, a vertical intermediate line is interpolated to derive respective positions of the patches. More specifically, for example, in the processing S12, the vertical edge lines depicted in FIG. 20 are derived, and, in the processing S13, an inter-vertical edge line interval histogram depicted in FIG. 21 is derived with respect to the vertical edge lines depicted in FIG. 20.

As mentioned above, the number of properly-detected vertical edge lines is considered to be generally greater than the number of undetected and erroneously-detected vertical edge lines. Thus, in one or more embodiments, in the processing S13, an average of inter-vertical edge line interval values belonging to a class having the largest frequency (a median value in the class) is defined as a most-credible inter-vertical edge line interval $Dv0$, i.e., a true value $Dv0$. In FIG. 21, a frequency in a class equivalent to each of two inter-edge line intervals related to the erroneously-detected vertical edge due to the streak-like printing irregularity is one.

After the true inter-vertical edge line interval value $Dv0$ is derived in this manner, the patch position processing section 65 operates to determine whether or not a distance between adjacent two of the vertical edge lines is equal to the true inter-vertical edge line interval value $Dv0$, wherein the patch position processing section 65 operates to, when the distance between the adjacent vertical edge lines is determined to be equal to the true inter-vertical edge line interval value $Dv0$, derive an intermediate line between the adjacent vertical edge lines, in the same manner as described above. A histogram about intervals between the vertical intermediate lines is derived, and a true value $Lv0$ of the inter-vertical intermediate line interval is derived. After the true inter-vertical intermediate line interval value $Lv0$ is derived, an intermediate line is interpolated, as necessary. That is, through the above processing, only proper intermediate lines depicted in FIG. 22B are derived from the actually-derived vertical edge lines depicted in FIG. 20, and then, although a 4th intermediate line counted from a left endmost intermediate line on the drawing sheet is undetected in FIG. 22B, an intermediate line CLest is interpolated at a position of the 4th intermediate line, as depicted in FIG. 22A After deriving the vertical intermediate lines in the above manner and deriving horizontal intermediate lines in a similar manner, intersection points thereof are derived as respective positions (x, y) of the patches. Then, in the processing S15, a color of each patch is measured at the position of the patch, and a result of the measurement is output in the processing S16.

As mentioned above, in the color measurement device CM in accordance with one or more embodiments and a color measurement method used therewith (hereinafter abbreviated as "color measurement device CM and others"), edge information is derived from an image of a color chart CT by the edge information processing section 63, and an edge statistic is derived from the derived edge information by the edge statistic processing section 64. Then, based on the edge information and the edge statistic, respective positions of a plurality of patches are derived by the patch position processing section 65. That is, in the color measurement device CM and others in accordance with one or more embodiments, a position of each patch is derived based on the edge information and the edge statistic, instead of based only on the edge information. Thus, for example, erroneous detection of an edge, undetection of an edge or the like can be reduced, so that it becomes possible to more accurately detect the position of each patch and measure a color of each patch at more proper position.

In one or more embodiments, the edge information includes intervals between edge lines (inter-edge line intervals). Thus, the color measurement device CM and others in accordance with one or more embodiments can derive an edge statistic based on the inter-edge line intervals, and can determine, based on the statistic about the inter-edge line intervals, whether or not the inter-edge line intervals are proper. Then, the color measurement device CM and others in accordance with one or more embodiments can determine, from a result of the determination of properness of the inter-edge line intervals, whether or not the edge lines are proper. Therefore, the color measurement device CM and others in accordance with one or more embodiments can determine properness of the edge lines, so that it becomes possible to more accurately detect a position of each patch based on the edge lines to measure a color of the patch at a more proper position.

In one or more embodiments, the edge information includes intervals between intermediate lines (inter-intermediate line intervals). Thus, the color measurement device CM and others in accordance with one or more embodiments can derive an edge statistic based on the inter-intermediate line intervals, and can determine, based on the statistic about the inter-intermediate line intervals, whether or not the inter-intermediate line intervals are proper. Then, the color measurement device CM and others in accordance with one or more embodiments can determine, from a result of the determination of properness of the inter-intermediate line intervals, whether or not the intermediate lines are proper. Therefore, the color measurement device CM and others in accordance with one or more embodiments can determine properness of the intermediate lines, so that it becomes possible to more accurately detect a position of each patch based on the intermediate lines to measure a color of the patch at a more proper position.

In one or more embodiments, a histogram about the edge information is derived. Thus, the color measurement device CM and others in accordance with one or more embodiments can determine most-credible edge information based on the derived edge information histogram. Then, the color measurement device CM and others in accordance with one or more embodiments can determine, using the most-credible edge information, whether or not the edge information is proper. Therefore, the color measurement device CM and others in accordance with one or more embodiments can determine properness of the edge information, so that it becomes possible to more accurately detect a position of each patch based on the edge information to measure a color of the patch at a more proper position.

As one example, in the case where a histogram about intervals between edge lines (inter-edge line interval histogram) is derived as the edge statistic is, the color measurement device CM and others derives the inter-edge line interval histogram, so that it can derive a most-creditable inter-edge line interval, based on the derived inter-edge line interval histogram. Then, the color measurement device CM and others can determine, using the most-credible inter-edge line interval, whether or not the edge lines are proper. Therefore, the color measurement device CM and others can determine properness of the edge lines, so that it becomes possible to more accurately detect a position of each patch based on the edge lines to measure a color of the patch at a more proper position.

As another example, in the case where a histogram about intervals between intermediate lines (inter-intermediate line interval histogram) is derived as the edge statistic, the color measurement device CM and others derives the inter-intermediate line interval histogram, so that it can derive a most-creditable inter-intermediate line interval, based on the derived inter-intermediate line interval histogram. Then, the color measurement device CM and others can determine, using the most-credible inter-intermediate line interval, whether or not the intermediate lines are proper. Therefore, the color measurement device CM and others can determine properness of the intermediate lines, so that it becomes possible to more accurately detect a position of each patch based on the intermediate lines to measure a color of the patch at a more proper position.

Figure 23:
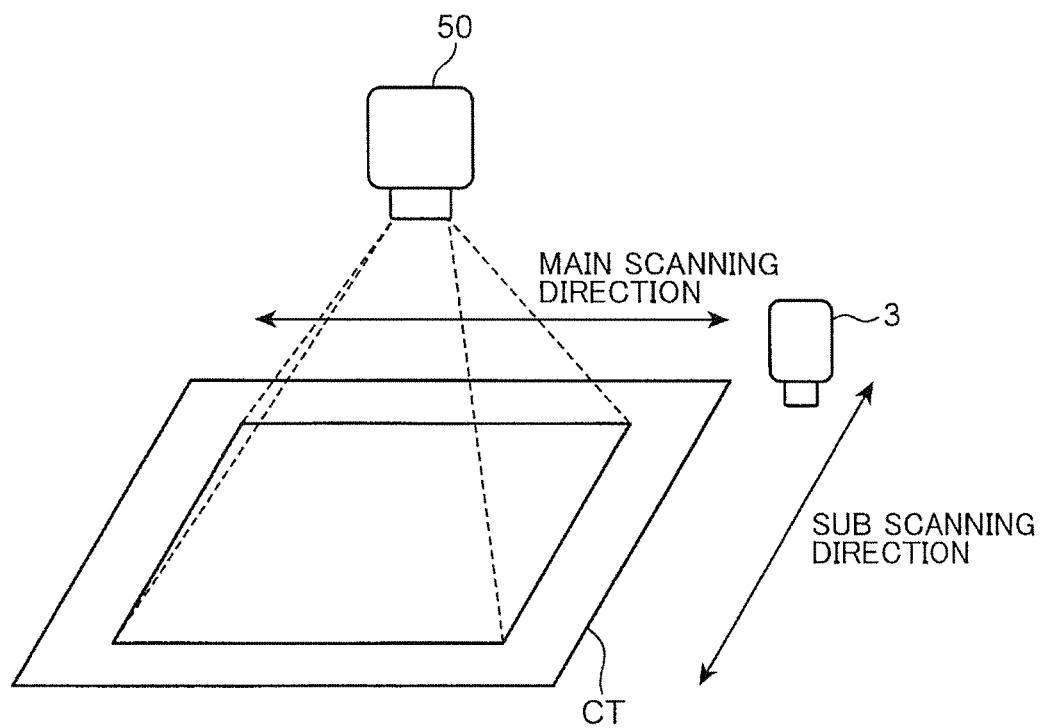
FIG. 23 is a diagram depicting a schematic configuration of a color measurement device in accordance with one or more embodiments of the invention, wherein the imaging unit comprises an area sensor.

In one or more embodiments, the color measurement device CM is equipped with the imaging unit 5 constructed such that it includes a liner sensor having a plurality of photoelectric conversion elements arranged along one direction. Alternatively, it may be equipped with an imaging unit 50 constructed such that it includes a two-dimensional image sensor, instead of the imaging unit 5. FIG. 23 is a diagram depicting a schematic configuration of a color measurement device in accordance with one or more embodiments, wherein the imaging unit comprises a two-dimensional image sensor. As depicted in FIG. 23, the imaging unit 50 constructed such that it includes a two-dimensional image sensor is capable of imaging an image of a color chart CT without conveying the color chart CT as mentioned above. Thus, this color measurement device CM may be simply constructed such that the color measuring unit 3 can be scanningly moved two-dimensionally with respect to the color chart CT. For example, the color measurement device CM may be constructed such that it includes a moving unit capable of moving the color measuring unit 3 in the main scanning direction (x-direction) and the sub scanning direction, or may be constructed such that it comprises a stage capable of allowing the color chart CT to be placed thereon and movable in the main scanning direction (x-direction) and the sub scanning direction. Alternatively, the color measuring unit 3 may be constructed to be movable in one of the main scanning direction and the sub scanning direction, and the stage may be constructed to be movable in the other direction.

This specification discloses various techniques as mentioned above. Among them, major techniques will be outlined as follows.

According to one aspect, there is provided a color measurement device which includes: a color measuring unit which measures a color; an imaging unit which acquires an image; an image acquisition processing section which causes the imaging unit to image a color chart having a plurality of patches each of which is a region of a given color, to thereby acquire an image of the color chart; an edge information processing section which derives given information regarding an edge as edge information, based on the image of the color chart acquired by the image acquisition processing section; an edge statistic processing section which statistically processes the edge information derived by the edge information processing section, to thereby derive a given statistic regarding the edge as an edge statistic; a patch position processing section which derives respective positions of the plurality of patches, based on the edge information derived by the edge information processing section and the edge statistic derived by the edge statistic processing section; and a color measurement processing section which causes the color measuring unit to measure respective colors of the plurality of patches, at the respective positions of the plurality of patches derived by the patch position processing section.

In the color measurement device having this feature, edge information is derived from the image of the color chart by the edge information processing section, and an edge statistic is derived from the derived edge information by the edge statistic processing section. Then, based on the edge information and the edge statistic, respective positions of the plurality of patches are derived by the patch position processing section. That is, in the color measurement device, a position of each patch is derived based on the edge information and the edge statistic, instead of based only on the edge information. Thus, for example, erroneous detection of an edge, undetection of an edge or the like can be reduced, so that it becomes possible to more accurately detect the position of each patch and measure a color of each patch at more proper position.

In one or more embodiments of the above color measurement device, the edge information includes one or more intervals between edge lines. Preferably, in this color measurement device, the edge information processing section is operable: based on the image of the color chart acquired by the image acquisition processing section, to derive one or more edge lines; and, when the number of the derived edge lines is plural, to derive, as the edge information, one or more intervals between the plurality of derived edge lines. Preferably, the one or more intervals between the edge lines are one or more distances between adjacent ones of the edge lines.

In this color measurement device, the edge information includes intervals between edge lines (inter-edge line intervals). Thus, the color measurement device can derive an edge statistic based on the inter-edge line intervals, and can determine, based on the statistic about the inter-edge line intervals, whether or not the inter-edge line intervals are proper. Then, this color measurement device can determine, from a result of the determination of properness of the inter-edge line intervals, whether or not the edge lines are proper. Therefore, this color measurement device can determine properness of the edge lines, so that it becomes possible to more accurately detect a position of each patch based on the edge lines to measure a color of the patch at a more proper position.

In one or more embodiments of the above color measurement device, the edge information includes one or more intervals between lines each intermediate between adjacent edge lines. Preferably, in this color measurement device, the edge information processing section is operable: based on the image of the color chart acquired by the image acquisition processing section, to derive one or more edge lines; when the number of the derived edge lines is plural, to derive one or more lines each intermediate between adjacent two of the plurality of derived edge lines; and, when the number of the derived intermediate lines is plural (when the number of the derived edge lines is three or more), to derive, as the edge information, one or more intervals between the plurality of derived intermediate lines. Preferably, the one or more intervals between the intermediate lines are one or more distances between adjacent ones of the intermediate lines.

In this color measurement device, the edge information includes intervals between intermediate lines (inter-intermediate line intervals). Thus, the color measurement device can derive an edge statistic based on the inter-intermediate line intervals, and can determine, based on the statistic about the inter-intermediate line intervals, whether or not the inter-intermediate line intervals are proper. Then, this color measurement device can determine, from a result of the determination of properness of the inter-intermediate line intervals, whether or not the intermediate lines are proper. Therefore, this color measurement device can determine properness of the intermediate lines, so that it becomes possible to more accurately detect a position of each patch based on the intermediate lines to measure a color of the patch at a more proper position.

In one or more embodiments of the above color measurement device, the statistical processing includes deriving a histogram about the edge information.

This color measurement device derives a histogram about the edge information, so that it can determine most-credible edge information based on the derived edge information histogram. Then, this color measurement device can determine, using the most-credible edge information, whether or not the edge information is proper. Therefore, this color measurement device can determine properness of the edge information, so that it becomes possible to more accurately detect a position of each patch based on the edge information to measure a color of the patch at a more proper position.

Preferably, in the above color measurement device, the edge information processing section is operable: based on the image of the color chart acquired by the image acquisition processing section, to derive one or more edge lines; and when the number of the derived edge lines is plural, to derive, as the edge information, one or more intervals between adjacent ones of the plurality of derived edge lines, and the edge statistic processing section is operable to derive, as the edge statistic, an inter-edge line interval histogram from the intervals derived by the edge information processing section. This color measurement device derives the inter-edge line interval histogram, so that it can derive a most-creditable inter-edge line interval, based on the derived inter-edge line interval histogram. Then, this color measurement device can determine, using the most-credible inter-edge line interval, whether or not the edge lines are proper. Therefore, this color measurement device can determine properness of the edge lines, so that it becomes possible to more accurately detect a position of each patch based on the edge lines to measure a color of the patch at a more proper position.

Preferably, in the above color measurement device, the edge information processing section is operable: based on the image of the color chart acquired by the image acquisition processing section, to derive one or more edge lines; when the number of the derived edge lines is plural, to derive one or more intermediate lines between adjacent two of the plurality of derived edge lines; and, when the number of the derived intermediate lines is plural (when the number of the derived edge lines is three or more), to derive, as the edge information, one or more intervals between the plurality of derived intermediate lines, and the edge statistic processing section is operable to derive, as the edge statistic, an inter-intermediate line interval histogram from the intervals derived by the edge information processing section. This color measurement device derives the inter-intermediate line interval histogram, so that it can derive a most-creditable inter-intermediate line interval, based on the derived inter-intermediate line interval histogram. Then, this color measurement device can determine, using the most-credible inter-intermediate line interval, whether or not the intermediate lines are proper. Therefore, this color measurement device can determine properness of the intermediate lines, so that it becomes possible to more accurately detect a position of each patch based on the intermediate lines to measure a color of the patch at a more proper position.

In one or more embodiments of the above color measurement device, the statistical processing comprising deriving an average value of the edge information belonging to each class in the histogram. Preferably, in this color measurement device, the edge statistic processing section is operable to derive, as most-credible edge information, an average value in one class having the largest (highest) frequency in the edge information histogram.

This makes it possible to provide a color measurement device in which an average value of the edge information belonging to a class is used as the edge information.

According to another aspect of the present invention, there is provided a color measurement method which includes: an image acquisition processing step of imaging, by an imaging unit, a color chart having a plurality of patches each of which is a region of a given color, to thereby acquire an image of the color chart; an edge information processing step of deriving given information regarding an edge as edge information, based on the image of the color chart acquired in the image acquisition processing step; an edge statistic processing step of statistically processing the edge information derived in the edge information processing step, to thereby derive a given statistic regarding the edge as an edge statistic; a patch position processing step of deriving respective positions of the plurality of patches, based on the edge information derived in the edge information processing step and the edge statistic derived in the edge statistic processing step; and a color measurement processing step of measuring, by a color measuring unit, respective colors of the plurality of patches, at the respective positions of the plurality of patches derived in the patch position processing step.

In the color measurement method having this feature, edge information is derived from the image of the color chart through the edge information processing step, and an edge statistic is derived from the derived edge information through the edge statistic processing step. Then, based on the edge information and the edge statistic, respective positions of the plurality of patches are derived through the patch position processing step. That is, in the color measurement method, a position of each patch is derived based on the edge information and the edge statistic, instead of based only on the edge information. Thus, for example, erroneous detection of an edge, undetection of an edge or the like can be reduced, so that it becomes possible to more accurately detect the position of each patch and measure a color of each patch at more proper position.

This application is based on Japanese Patent Application Serial No. 2014-99245 filed in Japan Patent Office on May 13, 2014, the contents of which are hereby incorporated by reference.

Although the present invention has been described appropriately and fully by way of the embodiments above with reference to the drawings in order to express the present invention, it should be appreciated that anyone skilled in the art can readily change and/or modify the embodiments described above. It is therefore understood that any changed embodiments or modified embodiments implemented by anyone skilled in the art is encompassed within the scope of the appended claims unless the changed embodiments or the modified embodiments are of a level that deviates from the scope of the appended claims.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

INDUSTRIAL APPLICABILITY

The present invention can provide a color measurement device and a color measurement method.

The invention claimed is:

1. A color measurement device comprising:
a color measuring sensor that measures a color;
an imaging sensor that acquires images;
a processor that:
  causes the imaging sensor to obtain an image of a color chart including a plurality of patches, each including a region of a given color;
  obtains edge information based on an edge of the image of the color chart;
  obtains edge statistic information of the edge by statistically processing the edge information;
  obtains position information of each of the plurality of patches based on the edge information and the edge statistic information; and
  causes the color measuring sensor to measure the given color of each of the plurality of patches at a position of each of the plurality of patches of the color chart using the position information.

2. The color measurement device as recited in claim 1, wherein the edge information obtained by the processor comprises an interval between edge lines of the color chart.

3. The color measurement device as recited in claim 2, wherein the statistical processing performed by the processor comprises obtaining a histogram of the edge information, wherein the histogram comprises a plurality of classes.

4. The color measurement device as recited in claim 3, wherein the statistical processing performed by the processor further comprises deriving an average value of each class of the histogram of the edge information.

5. The color measurement device as recited in claim 1, wherein the edge information obtained by the processor comprises an interval between lines that are each intermediate between adjacent edge lines of the color chart.

6. The color measurement device as recited in claim 5, wherein the statistical processing performed by the processor comprises obtaining a histogram of the edge information, wherein the histogram comprises a plurality of classes.

7. The color measurement device as recited in claim 6, wherein the statistical processing performed by the processor further comprises deriving an average value of each class of the histogram of the edge information.

8. A color measurement method using a color measurement device equipped with a color measuring sensor, an imaging sensor, and a processor, the method comprising:
  obtaining, by the imaging sensor, an image of a color chart including a plurality of patches, each including a region of a given color;
  obtaining, by the processor, edge information of an edge of the color chart based on the image of the color chart;
  obtaining, by the processor, edge statistic information by statistically processing the edge information;
  obtaining, by the processor, position information of each of the plurality of patches based on the edge information and the edge statistic information; and
  measuring, by the color measuring sensor, the given color of each patch of the plurality of patches at a position of each patch of the plurality of patches of the color chart using the patch information.

* * * * *